(12) United States Patent
Steiner et al.

(10) Patent No.: US 10,852,284 B2
(45) Date of Patent: Dec. 1, 2020

(54) METHOD AND DEVICE FOR OPTICAL IN OVO SEX DETERMINATION OF FERTILIZED AND INCUBATED BIRDS' EGGS

(71) Applicant: TECHNISCHE UNIVERSITAET DRESDEN, Dresden (DE)

(72) Inventors: Gerald Steiner, Schwarzenberg (DE); Grit Preusse, Radebeul (DE); Roberta Galli, Dresden (DE); Edmund Koch, Dresden (DE)

(73) Assignee: TECHNISCHE UNIVERSITÄT DRESDEN, Dresden (DE)

(*) Notice: Subject to any disclaimer, the term of this patent is extended or adjusted under 35 U.S.C. 154(b) by 214 days.

(21) Appl. No.: 16/090,947

(22) PCT Filed: Mar. 20, 2017

(86) PCT No.: PCT/EP2017/056536
§ 371 (c)(1),
(2) Date: Mar. 29, 2019

(87) PCT Pub. No.: WO2017/174337
PCT Pub. Date: Oct. 12, 2017

(65) Prior Publication Data
US 2019/0383782 A1    Dec. 19, 2019

(30) Foreign Application Priority Data
Apr. 4, 2016    (DE) .................. 10 2016 004 051

(51) Int. Cl.
*G01N 33/08*    (2006.01)
*A01K 41/00*    (2006.01)
(Continued)

(52) U.S. Cl.
CPC ............. *G01N 33/08* (2013.01); *A01K 41/00* (2013.01); *A01K 43/00* (2013.01); *A01K 45/007* (2013.01);
(Continued)

(58) Field of Classification Search
CPC ........ A01K 41/00; A01K 43/00; A01K 43/04; A01K 45/00; A01K 45/007;
(Continued)

(56) References Cited

U.S. PATENT DOCUMENTS 6,029,080 A    2/2000    Reynnells et al.
6,365,339 B1    4/2002    Daum et al.
(Continued)

FOREIGN PATENT DOCUMENTS

DE    10 2007 013 107    9/2008
DE    10 2010 006 161    1/2011
(Continued)

OTHER PUBLICATIONS

Fritz-Albert Popp, "Properties of biophotons and their theoretical implications", Indian Journal of Experimental Biology 41, 2003, pp. 391-402.
(Continued)

*Primary Examiner* — Hina F Ayub
(74) *Attorney, Agent, or Firm* — Greenblum & Bernstein, P.L.C.

(57) ABSTRACT

Method and a device for the optical in ovo sex determination of fertilized and incubated birds' eggs. The method includes monitoring formation of at least one identifiable blood vessel, creating a hole in the shell of the egg, finding and irradiating the blood vessel with at least one laser beam source emitting an excitation wavelength, recording backscatter radiation of the irradiated blood vessel and evaluating backscatter radiation from recorded spectral intensity of
(Continued)

fluorescence radiation in a spectral range redshifted to an excitation wavelength. Sex-specific properties of male and female blood are contained in the intensity and spectral profile of the recorded fluorescence radiation. where intensity levels for male blood has an evaluable value distinct from that of female blood. Further, determining the sex of the bird egg from difference values of the fluorescence intensity and displaying the sex determined for the embryo in the egg.

23 Claims, 9 Drawing Sheets

(51) Int. Cl.
    *A01K 43/00* (2006.01)
    *A01K 45/00* (2006.01)
    *G01N 21/64* (2006.01)
    *G01N 21/65* (2006.01)

(52) U.S. Cl.
    CPC ..... *G01N 21/6408* (2013.01); *G01N 21/6486* (2013.01); *G01N 21/65* (2013.01); *G01N 2021/6419* (2013.01); *G01N 2021/6421* (2013.01); *G01N 2333/465* (2013.01)

(58) Field of Classification Search
    CPC ... G01N 2021/6419; G01N 2021/6421; G01N 21/6408; G01N 21/6486; G01N 21/65; G01N 2333/465; G01N 33/08
    See application file for complete search history.

(56) References Cited

U.S. PATENT DOCUMENTS

| | | |
|---|---|---|
| 6,506,570 B1 | 1/2003 | Phelps |
| 7,041,439 B2 | 5/2006 | Phelps et al. |
| 7,950,349 B1 | 5/2011 | Rollins |
| 8,364,247 B2 | 1/2013 | Opitz et al. |
| 2011/0053210 A1 | 3/2011 | Matsumoto et al. |
| 2011/0144473 A1 | 6/2011 | Opitz et al. |
| 2012/0058052 A1 | 3/2012 | Decuypere et al. |
| 2013/0044210 A1 | 2/2013 | Rozenboim et al. |
| 2014/0308697 A1 | 10/2014 | Ye et al. |
| 2014/0332697 A1 | 11/2014 | Salhi et al. |
| 2015/0260704 A1 | 9/2015 | Bruins et al. |

FOREIGN PATENT DOCUMENTS

| | | |
|---|---|---|
| DE | 10 2007 013 107 | 2/2011 |
| DE | 10 2012 023 947 | 6/2014 |
| DE | 20 2013 011 765 | 7/2014 |
| DE | 10 2014 010 150 | 1/2016 |
| EP | 2 336 751 | 12/2009 |
| EP | 2 473 030 | 11/2013 |
| EP | 2 405 740 | 12/2015 |
| WO | 2010/103111 | 9/2010 |
| WO | 2010/150265 A3 | 12/2010 |
| WO | 2014/021715 | 2/2014 |
| WO | 2016/000678 | 1/2016 |

OTHER PUBLICATIONS

Michael A. Grashorn et al., "Integrated Assessment of Quality of Chicken Organic Eggs by Measurement of Dark Luminescence", Pol. J. Food Nutr. Sci. 57 No. 4(A), 2007, pp. 191-194.
S. Klein et al., "Analysis of chicken embryonic development after removal of blastodermal cells for sexing", British Poultry Science (39), 1998, pp. 482-487.
J. Brake et al., "Egg handling and storage", Poultry science (76), 1997, pp. 144-151.
M. Aamir Aslam et al., "A reliable method for sexing unincubated bird eggs for studying primary sex ratio", Molecular Ecology Resources, Bd. 12, Nr. 3, May 1, 2012, pp. 421+427.
Brigitte Osterath, "Forscher blicken ins Hühnerei", www.dw.com/de/forscher-blicken-ins-hühnerei/a-17015417, Apr. 17, 2014, pp. 1-5.
Susanne Dammers et al., "Raman-Spektroskopie", http://www.uni-muenster.de/imperia/md/content/physikalische_chemie/praktikum/raman_dammers_doedt.pdf, Jun. 6, 2005, pp. 1-32.
Kerstin Reiners et al., "Infrarot- und Ramanspektroskopie", http://www.greco.uni-oldenburg.de/Paper/InfrarotRamanVortrag.pdf, Jan. 1, 2003, pp. 1-88.
German Office Action conducted in counterpart German Appl. No. DE 10 2016 004 051.3 (dated Feb. 7, 2017).
Int'l Search Report (Form PCT/ISA/220 & 210) conducted in Int'l Appln. No. PCT/EP2017/056536 (dated Jun. 8, 2017).
Written Opinion (Form PCT/ISA/237) conducted in Int'l Appln. No. PCT/EP2017/056536 (dated Jun. 8, 2017) (w/ English translation).

Fig. 6
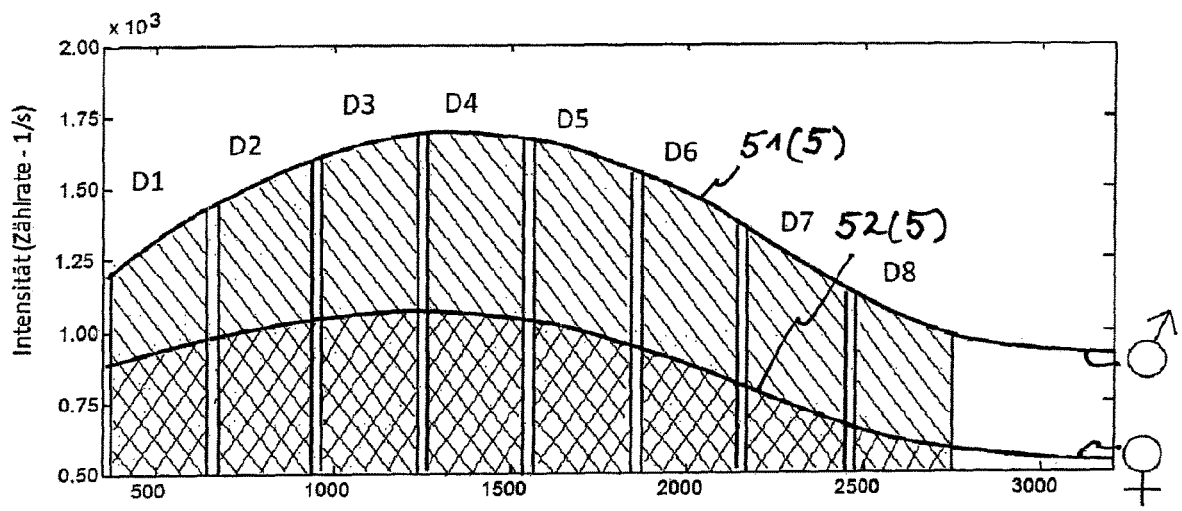
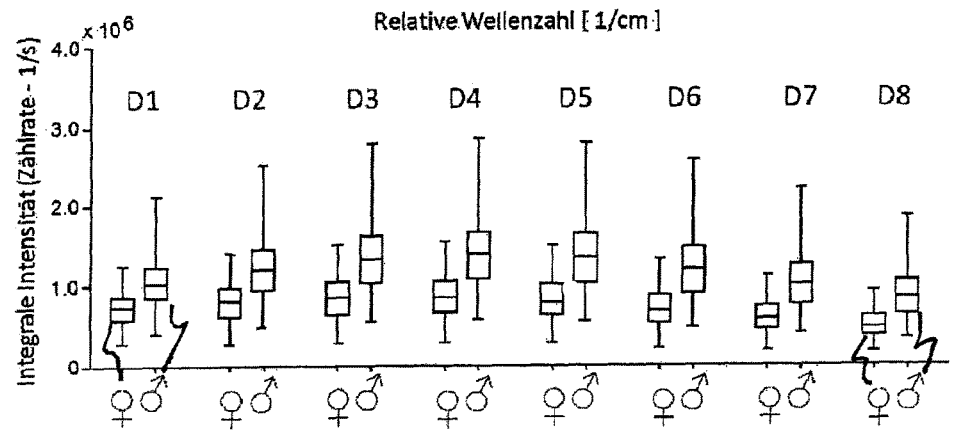
Fig. 6a
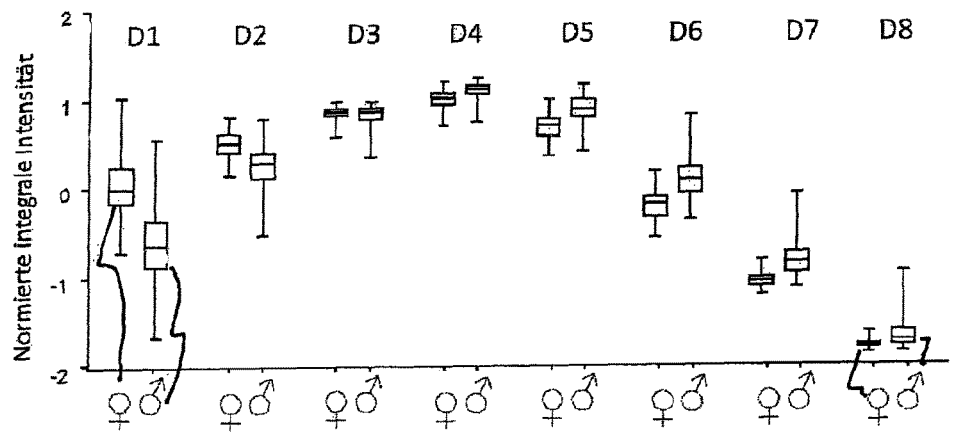
Fig. 6b

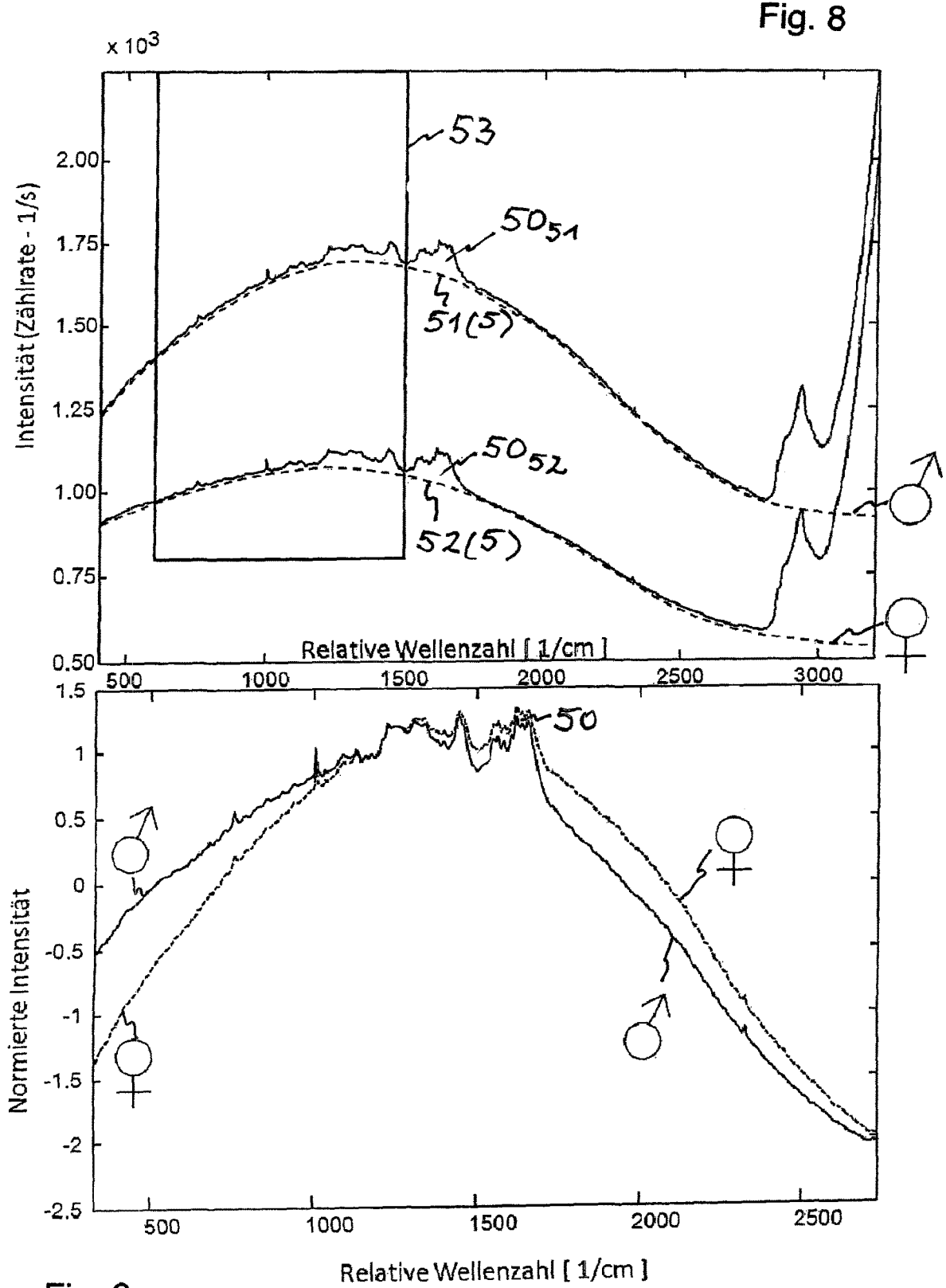

METHOD AND DEVICE FOR OPTICAL IN OVO SEX DETERMINATION OF FERTILIZED AND INCUBATED BIRDS' EGGS

The invention relates to a method and a device for the optical in ovo sex determination of fertilized and incubated birds' eggs.

In the documents DE 10 2014 010 150 A1 and WO 2016000678 A1, a method for the Raman spectroscopic in ovo sex determination of fertilized and incubated birds' eggs is described, wherein the embryo, including the extra-embryonic structures, can move in the egg and is not yet attached to the shell at the time of a measurement. The following steps are thereby carried out:

monitoring of the chronological progression of the incubation up to the formation of at least one identifiable blood vessel;

creation of a hole in the shell in the proximate region of the identified blood vessel by means of a hole-creating unit;

finding the blood vessels developing in the egg by means of a vision system and a coaxial or lateral illumination with light in the visible wavelength range;

positioning at least one blood vessel into the laser focus of a laser source, either by moving the egg or moving an objective lens of a device for introducing the laser light and detecting the Raman scattered radiation;

recording the Raman scattered radiation of the irradiated blood vessel by means of the device for introducing the laser light and for detecting the Raman scattered radiation, wherein during the measurement a movement of the blood vessel out of the focus can be prevented by means of tracking using the vision system.

evaluating the Raman scattered radiation and determining the sex in an evaluation unit;

displaying the sex of the embryo in the bird egg.

The Raman spectra are corrected such that background signals due to fluorescence or other scattering processes are eliminated and the spectra are normalized in a predetermined form before the mathematical analysis using methods of supervised and unsupervised classification.

In the documents U.S. Pat. No. 8,364,247 B2 and EP 2 336 751 A1, a method for determining the sex of birds' eggs is described in which, using a radiation source, electromagnetic radiation is emitted onto the germinal disc of an egg and, after the radiation source is switched off, the decay process of the excited intrinsic fluorescence intensity is detected at the irradiated region of the germinal disc in a time-resolved and spectrally resolved manner for at least one wavelength of the intrinsic fluorescence using a detector. Using the determined measured intensity values, the fractal dimension is calculated and the value of the fractal dimension DF is compared with a species- and sex-specific limit value; wherein the respective egg is classified as female if the limit value is exceeded and male if the value is lower than the limit value.

The method is used on germinal discs of fertilized birds' eggs, that is, at day "zero" of the incubation. The disadvantage of the method is that the opening of the egg at day "zero" results in markedly reduced hatching rates. Furthermore, there is a risk of potential irreparable damage to the germinal disc from the 337 nm UV radiation used.

In the document U.S. Pat. No. 7,950,349 B1, a method for determining 1) the fertility of a bird egg by measuring the luminescence and the biophoton intensity (photons per second) of the egg after exposure to an external light source and 2) the sex of a bird egg by measuring the photon spectrum of the biophoton emission and luminescence of the egg after exposure to an external light source is described.

The external light source can thereby be either an incandescent lamp, a fluorescent lamp, an LED, or a (pulsed or CW) monochromatic laser light source or dichromatic laser light source. The first part of the method results from the fact that, following exposure using the light source, the fertile birds' eggs emit a higher intensity of the photons than that emitted by the unfertilized birds' eggs. The second part of the method results from the fact that, following exposure using the indicated light sources, birds' eggs of the female sex emit a different spectrum of photons than birds' eggs of the male sex.

The disadvantages of the method are:

The luminescence is extremely weak and the measured intensities are only equal to a few to a few hundred photons per second and per square centimeter of surface area between 200 and 800 nm, as is described in the document Popp, Fritz: "Properties of biophotons and their theoretical implications", Indian Journal of Experimental Biology 41, 2003, p. 391-402.

A long exposure time is thereby necessary (30 s with a halogen lamp), as is described in the document Michael A. Grashorn, Ulrike Egerer: INTEGRATED ASSESSMENT OF QUALITY OF CHICKEN ORGANIC EGGS BY MEASUREMENT OF DARK LUMINESCENCE, Pol. J. Food Nutr. Sci. 2007, Vol. 57, No. 4(A), pp. 191-194.

In the documents WO 2010/150265 A3 and US 2013/0044210 A1, a method for the sex determination of non-incubated birds' eggs by means of a hyperspectral analysis of optical spectra, in particular reflection spectra, is described. The analysis takes place in a spectral range with wavelengths up to 2500 nm (MIR) in order to be able to filter out the signal generated by the calcium carbonate $CaCO_3$ of the eggshell at 2340 nm. The method enables the detection of biological components other than blood, and renders possible both the detection of fertility before the second incubation day and also the determination of the sex of the chicks in the egg at the twelfth incubation day. It is possible to increase the sensitivity through the use of a neural network analysis. By means of principal component analysis (PCA), the spectral characteristics that are responsible for the variances between the unfertilized control eggs and the sample eggs are determined. By employing a neural network analysis based on the PCA results, the small yet significant variances between the control eggs and the experimental eggs are then obtained. The method enables the determination of fertility with an accuracy of more than 90% at day "zero" (date of egg laying), and of the sex of the chicks with an accuracy of over 75% at the twelfth incubation day.

One disadvantage is that, with this method, a sex determination cannot be carried out until the twelfth day.

In the document DE 10 2007 013 107 B4, a DNA-relevant cell material is analyzed using vibrational spectroscopy in order to determine the sex of birds' eggs based on DNA differences: either in the egg opened using a probe, or after extraction of the material from the egg and deposition on a substrate. The UV resonance Raman spectroscopy is specified for wavelengths of 244 nm or 254 nm. A spectral classification is thereby carried out using all existing supervised and unsupervised methods:

with a DNA-relevant material, with a special reference to the feather pulp and the germinal disc, and UV Raman spectroscopy at a wavelength of 244 nm or 257 nm.

In this method, DNA-relevant cell material of the bird for which the sex is to be determined is thus examined using light and the molecular vibrations are measured, wherein the spectrum of the molecular vibrations produced by the light is detected and compared with predefined reference spectra as well as reference spectra representing sex-specific DNA structures of the bird species being examined, and wherein from said spectral comparison a sex is assigned to the bird based on the DNA content of the cell material.

The molecular vibrations are thereby measured using Raman spectroscopy or IR spectroscopy, wherein for example the DNA-relevant cell material can be extracted from the shaft of a young feather of a bird. The cell material is prepared on a slide and scanned using light. In another partial method described in the document DE 10 2007 013 107 A1, the light for measuring the molecular vibrations of the DNA-relevant cell material of unhatched birds is focused on the embryo or the germinal disc through the eggshell, wherein the spectrum of the radiation in the egg produced by the molecular vibrations is measured using a probe guided through the shell of said egg.

In order to guide the probe, at least one microscopically small hole is drilled through the eggshell to measure the spectrum. The light is focused through the small access point through the eggshell directly onto the germinal disc serving as cell material. The probe is inserted through the same access point or a different access point having a small opening size, by means of which probe the reflected spectrum of the aforementioned molecular motion in the interior of the egg, which spectrum is recorded by the probe, is measured.

The spectral information obtained is, in a second step, compared with sex-specific reference data and fed into a classification algorithm. Said data preferably represent statistically acquired data about the bird species being analyzed. From this comparison, a sex is assigned to the DNA material being analyzed.

One problem is that a significant cost in terms of time is required to insert a probe into preformed holes if a very high number of birds' eggs is to be analyzed. In addition, when the light from the probe is focused onto the germinal disc, considerable adjustment work must be performed for an optical mapping in relation to the location of the germinal disc, wherein the focal plane can have a different position for each egg, and it is thus not possible to carry out a sex determination.

A further problem with these analyses is that the creation of the holes in the shell, including the eggshell membrane, at day "zero" required to analyze the germinal discs results in an impairment of the embryonic development and in markedly decreasing hatching rates, as is described in the documents S. Klein: Analysis of chicken embryonic development after removal of blastodermal cells for sexing. British Poultry Science (39), 1998, p. 482-487; including the literature cited therein: J. Brake, T. W. (1997). Egg handling and storage. Poultry Science (76), p. 144-151.

For data processing, a first-order derivation and a vector normalization are performed, wherein all information about the fluorescence is eliminated.

In the document DE 10 2010 006 161 B3, a method and a device for determining the sex of fertilized and non-incubated birds' eggs are described, wherein an egg comprises at least a solid shell, an egg yolk surrounded by the shell and other egg integuments, and a germinal disc associated with the egg yolk, wherein a probe for measuring a spectrum is guided through a hole in the shell in the direction of the germinal disc having germinal disc cells, wherein the method comprises the following steps:

a positioning of the probe in the region of the germinal disc, a spectroscopic in ovo characterization of the germinal disc cells, a detection of the sex by means of an automatic classification of the reflective spectra, wherein an optical crystal is used as a probe, with which crystal a rapid and feedback-free recording of an infrared and/or near-infrared spectrum is performed through the evanescent field in the region of the germinal disc with the use of the attenuated total reflection inside the optical crystal, wherein the extinction takes place as a result of a spectral absorption of sex-specific germinal disc cells, wherein the positioning of the optical crystal is accompanied by a continuous automatic evaluation of the back-guided spectra until the sex-specific germination disc cells are determined, until the spectrum is evaluated and the sex of the fertilized egg is displayed unequivocally.

During the positioning process, continuously back-guided IR and/or NIR spectra are recorded and fed into an evaluation, wherein an automatic classification of the spectra takes place using the spectral fingerprint, for example in proteins, lipids and nucleic acids.

In the sex-specific absorption of the incident IR and/or NIR light, the germinal disc cells are identified using absorption bands of the nucleic acids (DNA and RNA) and other biochemical compounds such that the sex of the examined egg is determined and displayed.

The measurement can be conducted using conventional infrared spectroscopy.

The related device described in the document DE 10 2010 006 161 B3 contains at least one egg position support for securing at least one egg, at least one height-adjustment device having at least one supporting arm, at least one optical crystal embodied as a probe, which crystal is attached to the supporting arm, at least one control unit for the egg-securing egg position support and for the height-adjustment device, at least one spectral light source related to at least one wavelength range which emits an IR and/or NIR light beam, at least one detector for receiving the back-guided IR and/or NIR light beam, at least one optical element for the beam guidance guided between the light source and the optical crystal and for the beam guidance back-guided from the optical crystal to the detector, and an evaluation unit connected to the detector, as well as a display unit, wherein by means of the height-adjustment device the height of the supporting arm, and thus of the optical crystal, is adjustable in relation to the location of the germinal disc, and the optical crystal is positionable in the region of the germinal disc in a disc mapping position, in which an evanescent field which forms during total reflection at the output surface oriented toward the germinal disc is transferred to the germinal disc by means of the optical crystal, and the germinal disc cells located therein absorb in a sex-specific manner the light from the incident beam path interactively with the evanescent field, wherein the light totally reflected at the output surface is guided via the back-guided beam path within the crystal and is then guided via the optical element to the detector for recording, from which detector the recorded spectral signals for the evaluation and display of the sex are transmitted.

In the document WO 2014/021715 A2, a sex determination of bird embryos is described, wherein the method is carried out by means of
1) detection of a marker compound of sugars and amino acids, precursors and metabolites in the allantoic fluid of the egg at the eight to eleventh day of incubation,
2) quantitative determination of the marker using NMR spectroscopy,
3) sex determination by comparing the quantity of the marker to a predefined base value.

The following thereby take place:
a determination of the absolute quantities or proportions of compounds (glucose, choline, valine) in order to compare them with a base value, and
an application of unsupervised chemometric methods (such as least-square modeling or PCA) to quantitative amounts or proportions for the purpose of sex determination.

A major disadvantage of the method is that at least one sample is taken from the egg.

In the documents WO 2010/1031 11 A1 and US 2012/0058052 A1, a non-invasive method and a device for the in ovo sex determination of bird species are described. The method comprises the steps of introducing a labeled antibody into the egg, which antibody binds to a sex-specific antigen of the embryo, and the detection of the bound labeled antibody using a detection device outside the egg.

In the document U.S. Pat. No. 7,041,439 B2, a method and a device for the automated process management of eggs according to selected characteristics (for example, sex) are described, wherein the following steps take place:
a) an extraction of sample material (allantoic fluid, egg white, egg yolk, eggshell, albumin, tissue, membrane, and/or blood),
b) an analysis of the extracted material to determine the selected characteristics, and
c) selective process management for the identified eggs.

For example, a method for processing eggs based on the sex is described therein, which method comprises the following steps:
1) an identification of live eggs,
2) an extraction of allantoic fluid from the eggs identified as living,
3) a determination of the estrogen content and of a color change in the extracted allantoic fluid for the purpose of sex detection,
4) a selective injection of a vaccine depending on the sex.

One disadvantage is that the analysis of the allantoic fluid takes place at day 13 through 18. Sampling is also necessary in this case.

In the document U.S. Pat. No. 6,365,339 B1, a method for the sex determination of bird embryos is described in which, during the incubation process, samples are taken from the allantoic fluid of the embryo after the shell is drilled open and are analyzed in an ion mobility spectrometer (IMS). The resulting spectra contain relevant marker peaks which correlate with sex-specific mobilities. One disadvantage is that samples must also be taken in this case, which samples necessitate additional effort at least in the context of the sex determination.

In the document U.S. Pat. No. 6,029,080 B1, a non-invasive method and a device for the sex determination of birds' eggs is shown in which nuclear magnetic resonance (NMR) is used to determine whether the live embryo in the egg has male sex organs or female sex organs.

One disadvantage is that the formation of the sex organs only takes place in a developed embryo after several essential days, wherein at least the implementation requires a high financial cost.

In the document U.S. Pat. No. 6,506,570 B1, the presence or absence of an elevated sex-specific hormone level, preferably the estrogen level, is determined in an extra-embryonic fluid, preferably the allantoic fluid, for the purpose of in ovo sex determination of birds' eggs. The method is preferably applied to chicken eggs and can be carried out before or during the transfer from the incubator to the hatcher.

In the document DE 10 2012 023 947 A1, a method for structural elucidation through an optically non-transparent barrier of a biological test object is described. In the test object, an inner structure having different dielectric properties is elucidated by means of an electromagnetic spectral analysis,
wherein the test object is positioned below an array of pulse transmitters and receivers that are arranged on a plane and connected to a computer system such that data and information are transmitted,
wherein electromagnetic pulses in the spectral range of 0.01 THz to 1 THz are emitted onto the positioned test object by the pulse transmitters, wherein the radiation emitted from the test object is recorded by the receivers and fed to the computer via the data-transmitting and information-transmitting connections for an imaging process.

Since the THz radiation is very weak, long measurement times occur which are a hindrance to performing a rapid automatic sex determination. In addition, a high absorption of accompanying water vapor in the THz range requires an extremely low and consistent humidity in the hatchery, which in turn results in considerable additional technical work.

In the document DE 20 2013 011 765 U1, a spectrophotometric analysis of the feather color of chicken embryos is described. Electromagnetic energy with a wavelength between approximately 380 nm and 740 nm is thereby used for the non-invasive sex determination of bird embryos, wherein a bird egg is exposed to the electromagnetic energy and the amount of absorption, diffusion, refraction, reflection, or any desired combination thereof of the electromagnetic energy is determined through the bird egg. By means of the presence or absence of color pigment in the interior of the bird egg, the sex of the bird embryo is at least partially determined.

The spectrophotometric analysis of the feather color of chicken embryos can only be used on brown breeds or on breeds with a color difference between female chicks and male chicks.

A summary of the disadvantages of the methods from the documents cited is provided below:
1. The sex determination at day "zero" requires access to the identified position of the germinal disc, which from previous experience entails an impairment of embryonic development and markedly decreasing hatching rates.
2. In the case of late-stage sex determination at 7 to 21 days of incubation,
firstly, aspects of animal welfare legislation play a significant role;

wherein the bird embryo begins to experience pain starting on the seventh incubation day, and wherein a late-stage killing of highly developed bird embryos is carried out, since the egg contents comprise the bird embryo itself as incubation progresses; and secondly, economic aspects play a significant role;

wherein the male eggs are in the incubator longer for late-stage sex determination, which causes a substantially poorer capacity utilization of the incubators and therefore higher energy costs.

3. In the case of a sex determination using an extraction of sample material, the following problems may occur:

the additional cleaning and disinfection required after each measurement and/or the replacement of devices or device parts (e.g., tubes) increases ongoing consumption costs considerably, an automation capability is more limited than for non-contact methods, and the risk of infection is markedly increased, as a result of which there may be a danger of reduced hatching rates.

The manner in which an endogenous fluorescence of the blood—independent of the sex determination—is used in order to characterize blood is described below:

In the document US 2011/053210, a blood analyzer that is based on fluorescence measurement is described.

The blood analyzer comprises a sample preparation segment, a measuring sample from a blood sample and from a hemolytic agent, a light information unit which produces the fluorescence information and at least two types of scattered light information from the measuring sample, and a control unit for a first classification of the white blood cells in the measuring sample into at least four groups (including monocytes, neutrophils, eosinophils) on the basis of the information from the fluorescence signals and the signals of the two types of scattered light.

Disadvantages are that the blood analysis does not yield any information about the sex, but rather solely information about the blood cells. The blood analysis takes place not in situ in the blood vessel, but rather on separated blood samples. The excitation wavelength is between 350 nm and 500 nm. The signals are not evaluated spectroscopically; only an evaluation of the intensity of the backscattered and transmitted light takes place.

In the document US 2014/332697, a method for spectral detection techniques of blood a1 components according to thalassemia is described, which method is based on fluorescence spectra of biomolecules. Biomolecules include, among other things, tyrosine, tryptophan, nicotinamide adenine dinucleotide and flavin adenine dinucleotide, all of which are found in blood plasma, as well as porphyrin from the erythrocytes. In this method, the ratios of the intensity maxima between tryptophan, nicotinamide adenine dinucleotide, flavin adenine dinucleotide, nicotinamide adenine dinucleotide, tyrosine, tryptophan, and porphyrin are used in order to diagnose a patient with thalassemia.

The disadvantages are that the analysis takes place not in situ in the blood vessel, but rather on separated blood samples. The excitation takes place in the UV range; the recording of the fluorescence signals takes place in the UV and VIS range between 350 nm and 500 nm.

In the document US 2014/0308697 A1, methods and devices for identifying erythrocytes infected with plasmodium are described. The methods comprise:

obtaining a forward scatter light signal, a side scatter light signal, and an optional fluorescence signal of cells in a blood sample;

obtaining a two-dimensional scattergram (forward scatter light signal and side scatter light signal) or a three-dimensional scattergram (forward scatter light signal, side scatter light signal, and fluorescence signal);

identifying erythrocytes infected with plasmodium as cells that are located in a predetermined region of the two-dimensional scattergram or of the three-dimensional scattergram.

The object of the invention is to specify a method and a device for the optical in ovo sex determination of fertilized and incubated birds' eggs, which method and device are suitably embodied such that the sex can already be determined in the eggs in a rapid and reliably unequivocal manner. The female embryo is to continue developing normally, and the female chick is to be hatched.

The object is attained by the features of patent claims 1 and 14.

In the method for the optical in ovo sex determination of fertilized and incubated birds' eggs, the following steps are carried out:

monitoring the chronological progression of the incubation until at least one identifiable blood vessel develops with flowing blood;

creating a hole in the shell of the bird egg by means of a hole-creating unit;

finding the blood vessels developing in the egg, or finding the heart, using a vision system and a coaxial or lateral illumination with light in the visible wavelength range;

positioning at least one blood vessel or the heart in the laser focus of at least one laser beam source, either by moving the egg or by moving an objective lens that produces the laser focus;

irradiating the blood vessel or the heart with at least one laser beam source emitting an excitation wavelength;

recording the backscatter radiation of the irradiated blood vessel or the heart using at least one detector that is connected to at least one evaluation unit connected to a downstream amplification and detector unit, wherein during the recording a movement of the blood vessel or the heart out of the laser beam can take place by a tracking of the blood vessels or the heart or the objective lens;

wherein according to the characterizing part of patent claim 1, the additional steps below follow evaluation of the backscatter radiation, including the fluorescence radiation, in the evaluation unit from the recorded spectral intensity of the fluorescence radiation in a spectral range redshifted to the excitation wavelength, wherein the sex-specific properties of the male blood and the female blood are contained in the intensity and in the spectral profile of the recorded fluorescence radiation, and wherein at least one of the intensity levels determined from the measured spectral intensities of the fluorescence radiation, or the values assigned thereto, for the male blood has an evaluable value distinct from at least one of the determined intensity levels, or the values assigned thereto, for the female blood in the blood vessels;

determination of the sex of the bird egg from the difference of at least one of the values of the fluorescence intensity levels, or the values assigned thereto, in the evaluation unit; and subsequently at least one display of the sex determined in the evaluation unit for the embryo in the bird egg.

The respectively evaluable distinct value for the intensity levels can at least be based on a predefined limit value or threshold value that is stored in the evaluation unit and assigned to the intensity level.

In the evaluation unit, the intensity levels determined for a predefined spectral range from the established fluorescence intensity/wavenumber curves can be defined as the integral intensity $I_{f51}$ of the fluorescence radiation of the male blood and as the integral intensity $I_{f52}$ of the fluorescence radiation of the female blood.

In the evaluation unit, the intensity levels determined for a predefined spectral range from the established fluorescence intensity/wavenumber curves can be defined as the intensity maximum $51_{Max}$ of the fluorescence radiation of the male blood and as the intensity maximum $52_{Max}$ of the fluorescence radiation of the female blood.

In the evaluation unit, if one laser beam source is used, the intensity levels determined for a predefined spectral range from the established fluorescence intensity/wavenumber curve can be respectively defined for the male blood and for the female blood such that they are combined by means of a logical operation for evaluation.

In the evaluation unit, if at least two laser beam sources are used, the intensity levels determined for a predefined spectral range from multiple established fluorescence intensity/wavenumber curves can be defined as the integral intensities $I_{f511}$, $I_{f512}$ of the fluorescence radiation of the male blood and as the integral intensities $I_{f521}$, $I_{f522}$ of the fluorescence radiation of the female blood.

In the evaluation unit, if at least two laser beam sources are used, the intensity levels determined for a predefined spectral range from the established fluorescence intensity/wavenumber curves can be respectively defined for the male blood and for the female blood such that they are combined for evaluation.

In the evaluation unit, the intensity levels determined for a predefined spectral range from the established fluorescence intensity/wavenumber curves can be defined as the integral intensity $I_{f51}$ of the fluorescence radiation of the male blood and as the integral intensity $I_{f52}$ of the fluorescence radiation of the female blood and the Raman scattered radiation $50_{51}$, $50_{52}$ respectively overlapping the fluorescence radiation can be defined for the evaluation alone or in combination with the other defined intensity levels and assigned values, wherein if the intensity levels and assigned values are combined, the Raman scattered radiation and the fluorescence radiation are evaluated together by means of a logical operation.

If a pulsed laser beam from the laser beam source is used, the fluorescence intensity generated can be measured in a time-resolved manner and, from the time constant $\tau$ of the decay curve for the time-resolved fluorescence intensity, a sex determination can be carried out, wherein a different time constant $\tau_{male}$, $\tau_{female}$, with $\tau_{male} \neq \tau_{female}$, is respectively determined for male blood and for female blood from the fluorescence decay curve in order to determine the sex.

If the likewise generated and recorded Raman scattered radiation is taken into consideration, the intensity levels determined for a predefined spectral range from the established fluorescence intensity/wavenumber curves can be defined in the evaluation unit as the integral intensity $I_{f51}$ of the fluorescence radiation of the male blood and as the integral intensity $I_{f52}$ of the fluorescence radiation of the female blood and the respective Raman scattered radiation $50_{51}$, $50_{52}$ overlapping the fluorescence radiation can be defined for the evaluation.

A device for the optical in ovo sex determination of a fertilized and incubated bird egg based on generated fluorescence radiation comprises
- an egg-mounting unit, on which the egg is mounted;
- a position-evaluation device which is connected to the egg-mounting unit;
- a radiation device with light in the visible wavelength range for irradiating at least one extra-embryonic blood vessel, one embryonic blood vessel, or the heart of the embryo;
- a detector for visible or green light for the detection of at least one extra-embryonic blood vessel, one embryonic blood vessel, or the heart of the embryo, wherein the detector is connected to the positioning evaluation device;
- a device for introducing laser light into the egg, which device is at least connected to
  - a laser source emitting laser light;
  - a detector for recording the fluorescence radiation;
  - a control unit for XYZ-positioning of the device onto the hole created in the egg;
  - a sex-determination evaluation unit that is connected to the amplification and detection unit and to the positioning evaluation unit, which is connected to the control unit;

wherein according to the characterizing part of patent claim 14, a device for separating the fluorescence radiation from the backscatter radiation is arranged between a collimator for collimating the laser beam and the device for introducing the laser beam into the egg, wherein between the beam-separating device and at least one fluorescence detector respectively one beam path-specific detection filter for the transmission of the fluorescence radiation is integrated, wherein the following take place in the sex-determination evaluation unit
- an evaluation of the backscatter radiation, including the fluorescence radiation, from the recorded spectral intensity of the fluorescence radiation in a spectral range redshifted to the excitation wavelength, wherein the sex-specific properties of the male blood and the female blood are contained in the intensity and in the spectral profile of the recorded fluorescence radiation, and wherein at least one of the intensity levels determined from the measured spectral intensities of the fluorescence radiation, or the values assigned thereto, for the male blood has an evaluable value distinct from at least one of the determined intensity levels, or the values assigned thereto, for the female blood in the blood vessels;
- a determination of the sex of the bird egg from the difference of at least one of the values of the fluorescence intensity levels, or the values assigned thereto, in the evaluation unit.

The light in the visible wavelength range, with which the radiation device is provided in order to irradiate at least one blood vessel, is preferably green light.

The laser beam that is produced in the laser can be transmitted by means of mirrors or by means of fiber optics. The laser beam is collimated using the collimator.

The laser beam is transmitted to the egg and, using a lens, focused onto an extra-embryonic blood vessel, an embryonic blood vessel, or the heart of the embryo.

The fluorescence radiation generated is collected using the same lens.

A beam splitter is used to separate the fluorescent signal from the visible light of the beam source.

The light in the visible spectral range is transmitted to the camera; a filter removes remaining beams of the laser light.

A beam splitter is used to separate the fluorescent light that strikes the detector. The detector, typically a photodiode, preferably an avalanche photodiode of a photomultiplier, measures the intensity of the fluorescence radiation.

At least one bandpass filter selects the spectral range to be measured for the fluorescence.

A detection unit amplifies, filters, and measures the signal from the detector, which signal is sent from the detection unit to the sex-determination unit.

The measured intensity is evaluated in the evaluation unit, for example, by means of a comparison with a measured threshold value TV, and the sex of the egg is thus determined.

The creation of a hole in the shell by means of a hole-creating unit in the form of a laser or by means of mechanical perforation can be carried out with diameters up to 18 mm, preferably between 4 mm and 15 mm. The light in the visible wavelength range can be white light, but the contrast is improved if blue and/or green light from a light source is used (for example, a green or blue LED, or an incandescent lamp with a blue or green filter). During the measurement, a movement of the blood vessel or the heart out of the laser beam can take place by a tracking of the blood vessels or the heart or the associated objective lens, activated by the monitoring vision system.

Fluorescence radiation measurements are conducted using optical systems such as lenses or microscope objective lenses or a fiber probe.

The focused or collimated laser beam is focused onto the selected blood vessel or onto the heart and, if necessary, the tracking is carried out automatically using a lens or an objective lens if the selected blood vessel or the heart moves.

The excitation wavelengths of the laser light from the laser beam source are greater than 400 nm, with the use of, e.g., an HeNe laser 633 nm, solid-state laser (Nd-based, e.g., Nd:YAG laser 532 nm or 1064 nm; VIS NIR diode laser, e.g., 785 nm). The coupling of the laser excitation beam can take place directly with mirrors and/or with optical fibers. The output introduced from the laser beam source must not result in a local or global heating of the egg above 40° Celsius.

A direct decoupling of the collected backscatter radiation takes place with mirrors or with optical fibers until detection. Part of the backscatter radiation contains the fluorescence radiation.

The fluorescence radiation can preferably be recorded using an objective lens.

The respective optical element for the beam guidance or for the back-guiding beam guidance can be a flexible optical fiber.

A detection of the backscatter radiation can be carried out as described below, by:
- using equipment which measures the light intensity or the photon flow, such as photodiodes, avalanche photodiodes, or photomultipliers, for example;
- using beam splitters and optical bandpass filters before detection, in order to select the spectral ranges of the fluorescence; or
- using dispersive spectrometers to conduct a spectral analysis.

The sex-specific features are contained in the intensity and in the spectral profile of the fluorescence, wherein the fluorescence intensities determined in one or more spectral ranges are fed to a mathematical analysis.

The sex determination can be performed at any day between the formation of at least one identifiable blood vessel, or the formation of the heart, and the hatching, preferably approximately at day 2.5 to day 5 of the incubation. After the fifth incubation day, the difference between the autofluorescence of the blood of male embryos and female embryos diminishes.

The advantages of the sex determination according to the invention are:
- no impairment of hatching and the subsequent development of the chick, and
- a performance of the sex determination in a highly accurate manner in real time, at a very early point and with the aid of non-contact determination without sampling.

The recorded spectral backscatter radiation is variable within the spectral range, but is always redshifted in comparison to the excitation wavelength of the laser. Typically, a frequency shift is between approx. 100 $cm^{-1}$ and 4000 $cm^{-1}$. In the spectral range, the autofluorescence of the blood is different for male embryos and for female embryos. The intensity of the autofluorescence of the male blood is stronger, and the spectral fluorescence maximum for the intensity of the male blood is slightly shifted to higher wavenumbers. The weak Raman radiation is overlaid onto the fluorescence radiation.

Four different configurations of the device according to the invention are illustrated below. The configurations are described for use with an egg; parallelizations of the device according to the invention, that is, an arrangement of multiple devices according to the invention in a sex-determination line, are possible in order to then be able to automatically analyze a higher number of eggs with regard to the sex within the same time span.

Developments and advantageous embodiments of the invention are specified in additional dependent claims.

The invention is explained in greater detail by means of exemplary embodiments with drawings.

Wherein:

FIG. 1 shows a schematic illustration of a first device according to the invention for determining the sex of incubated birds' eggs based on generated fluorescence radiation after excitation by means of a measurement of the integral intensity for the male sex and for the female sex of the embryo using a device for separating the fluorescence radiation and a detector, wherein FIG. 1a illustrates an enlarged view into the hole opening with the embryo, the accompanying blood vessels, and the extra-embryonic blood-carrying vessels according to FIG. 1;

FIG. 2 shows a schematic illustration of a second device according to the invention for determining the sex of incubated birds' eggs based on generated fluorescence radiation after excitation by means of a measurement at predefined wavenumbers using a device for separating the fluorescence radiation and a number of detectors;

FIG. 3 shows a schematic illustration of a third device according to the invention for determining the sex of incubated birds' eggs based on generated fluorescence radiation after excitation by means of at least two laser sources and the measurement of each of the two curves shown as integral intensities in FIG. 7 for the male sex and for the female sex of the embryo at predefined wavenumbers using a device for separating the fluorescence radiation and multiple detectors;

FIG. 5 shows fluorescence intensity/wavenumber curves for the first device according to the invention from FIG. 1 for determining the sex of incubated birds' eggs based on generated fluorescence radiation after excitation by means of a measurement of the integral intensity (each with different shading lines), wherein

Figure 2:
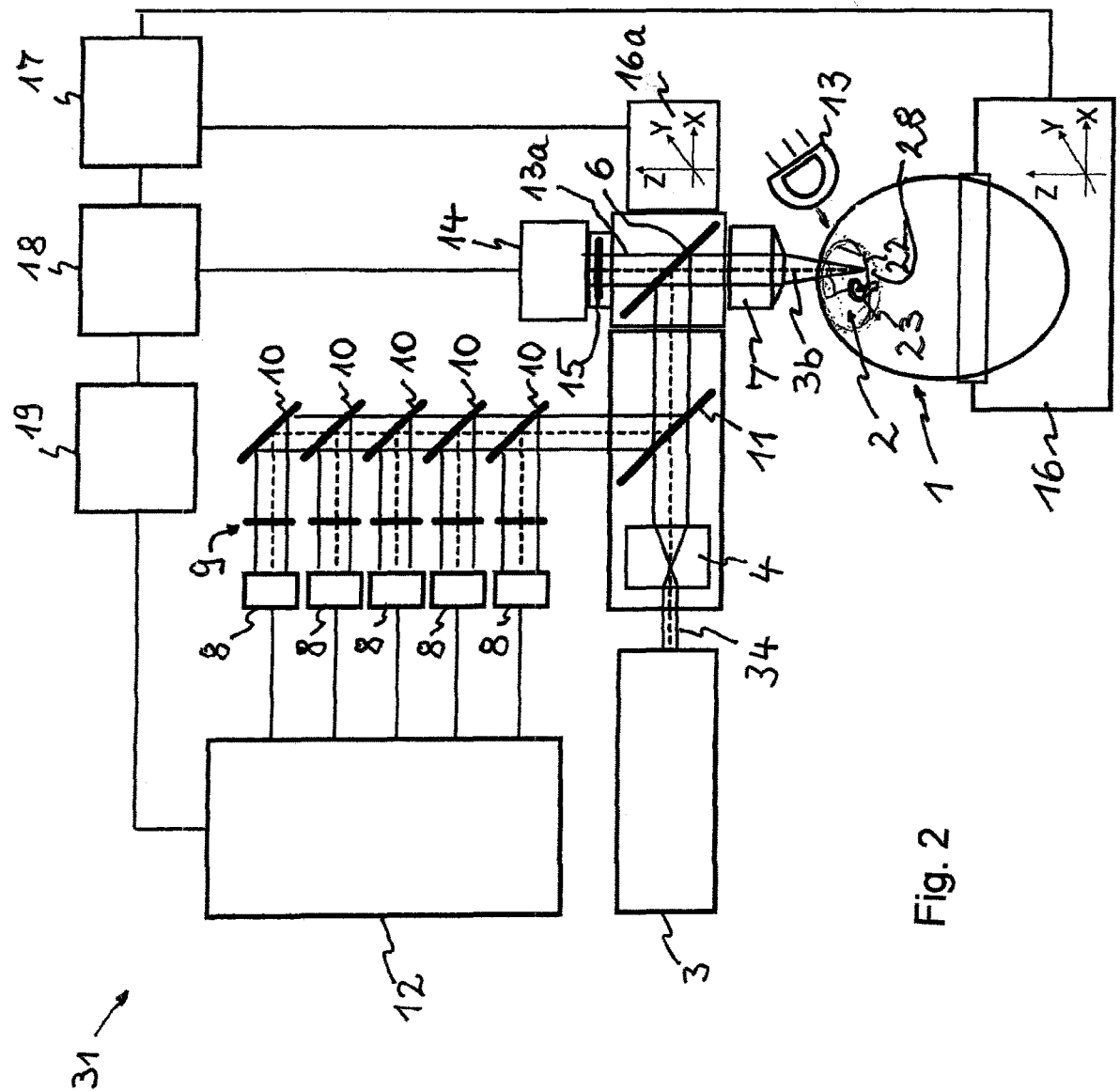
Figure 3:
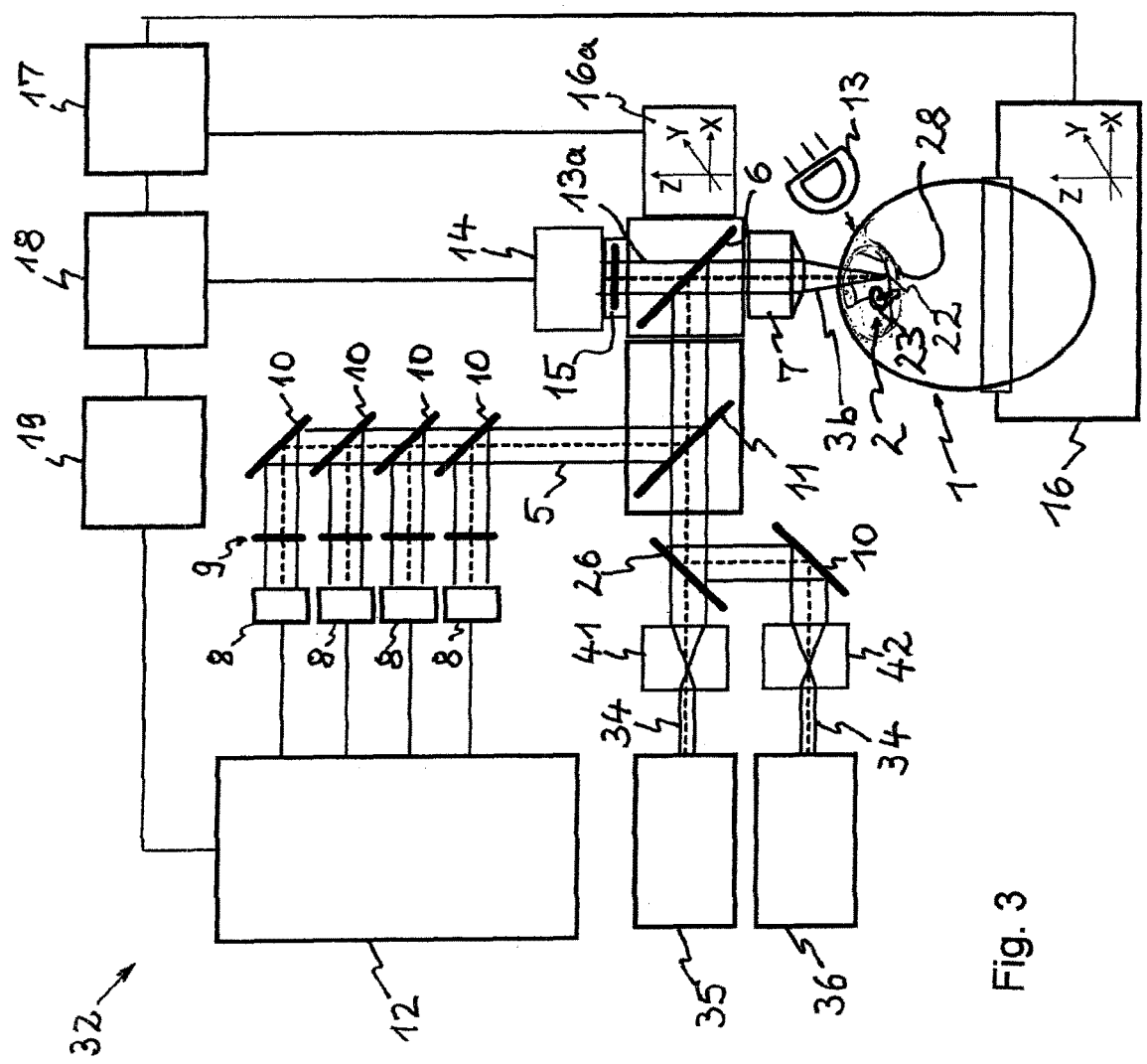
Figure 4:
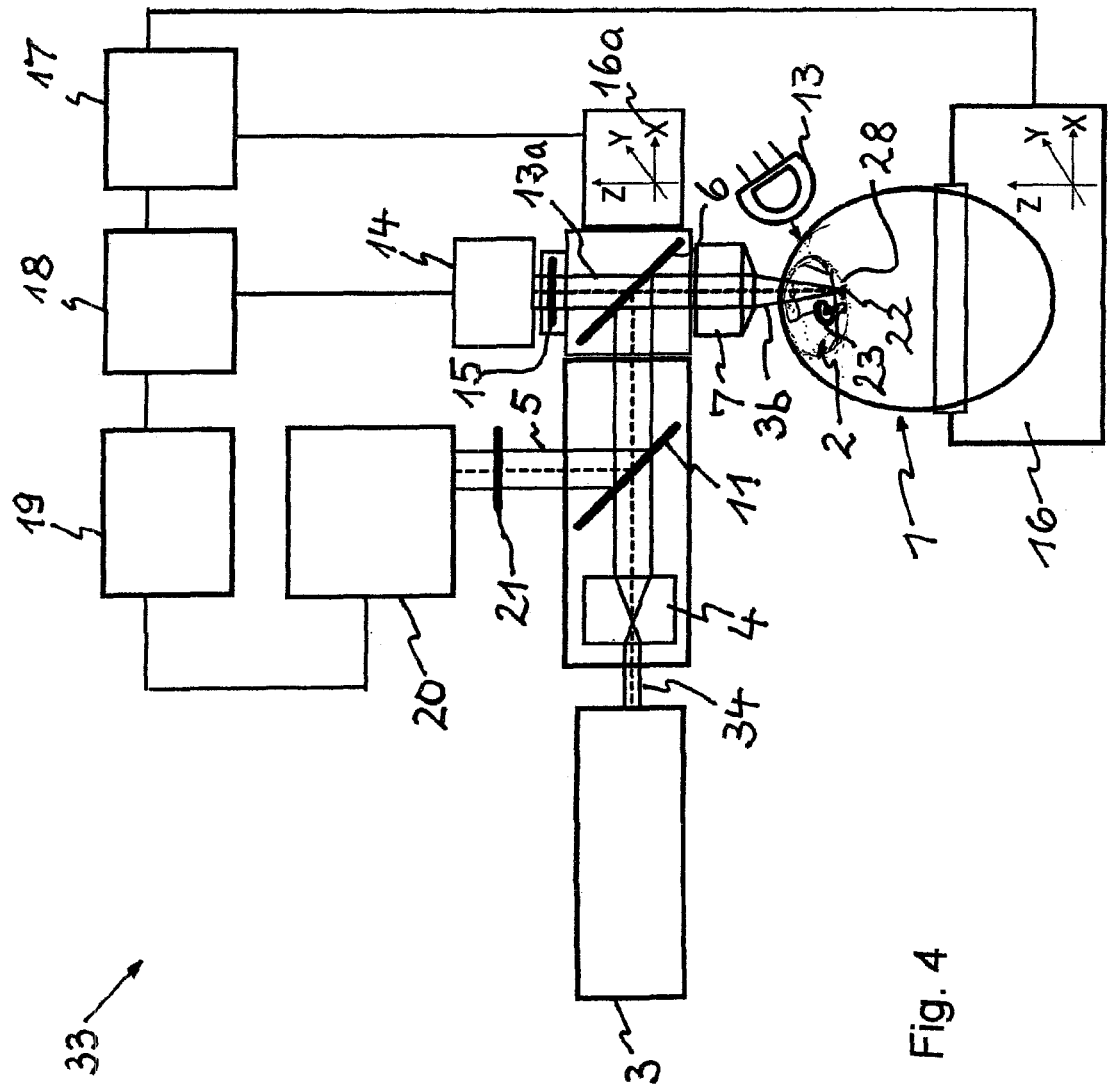
FIG. 4 shows a schematic illustration of a fourth device according to the invention for determining the sex of incubated birds' eggs based on generated fluorescence radiation and the Raman scattered radiation after excitation by means of the measurements of the two intensity curves using a device for separating the fluorescence radiation and a spectrometer.
Figure 7:
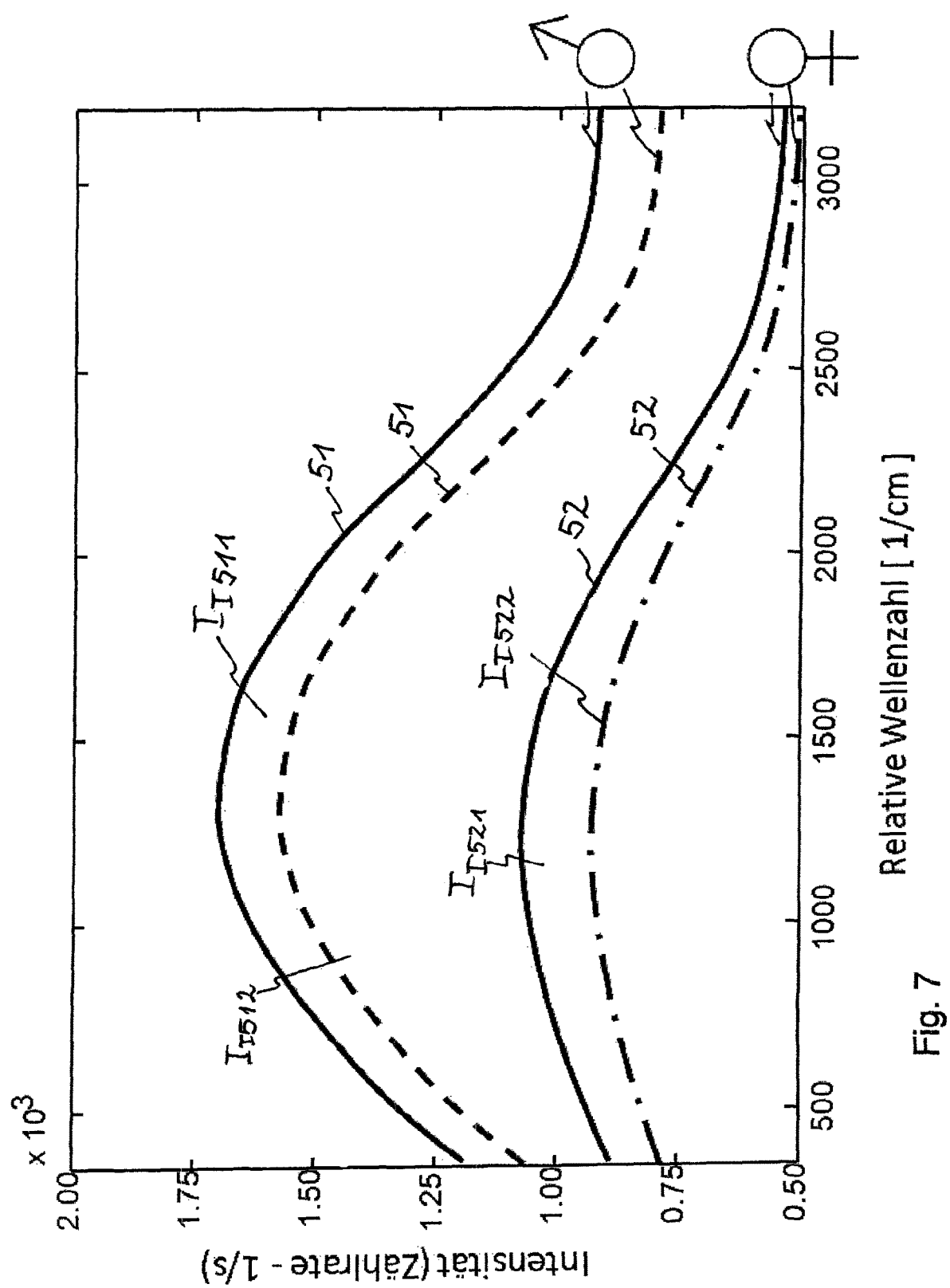

FIG. 6 shows fluorescence intensity/wavenumber curves for the second device according to the invention from FIG. 2 for determining the sex of incubated birds' eggs based on generated fluorescence radiation after excitation by means of a measurement of the intensity using the recorded intensity curves at respectively predefined wavenumbers, wherein FIG. 6a shows the integral intensities of defined partial spectral ranges over the entire spectral range; and FIG. 6b shows the normalized intensity from FIG. 6 and FIG. 6a;

FIG. 7 shows fluorescence intensity/frequency number curves for the third device according to the invention from FIG. 3 for determining the sex of incubated birds' eggs based on generated fluorescence radiation after excitation by means of two laser beam sources emitting different wavelengths with a measurement of the different intensity curves (solid and dashed, respectively);

FIG. 8 shows fluorescence intensity/frequency number curves for the fourth device according to the invention from FIG. 4 for determining the sex of incubated birds' eggs based on generated fluorescence radiation and Raman scattered radiation after excitation by means of a laser beam source for the measurement of the two overlapping intensities, wherein FIG. 8a shows the curves of the normalized intensities from FIG. 8.

Figure 1A:
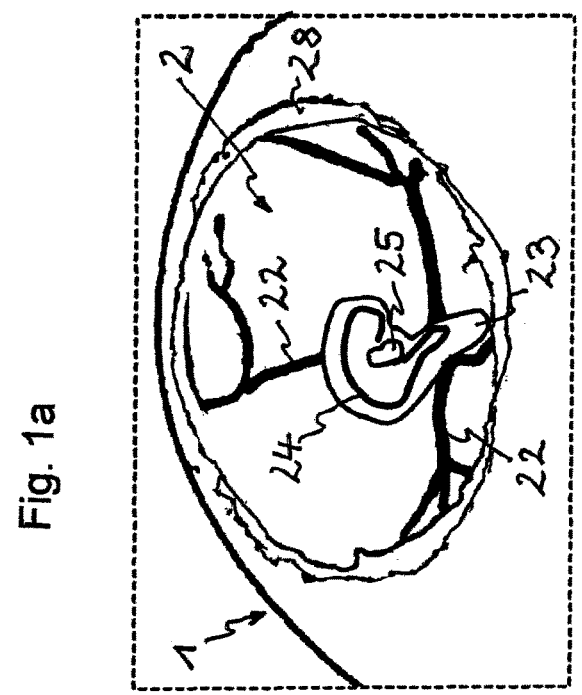
Figure 1:
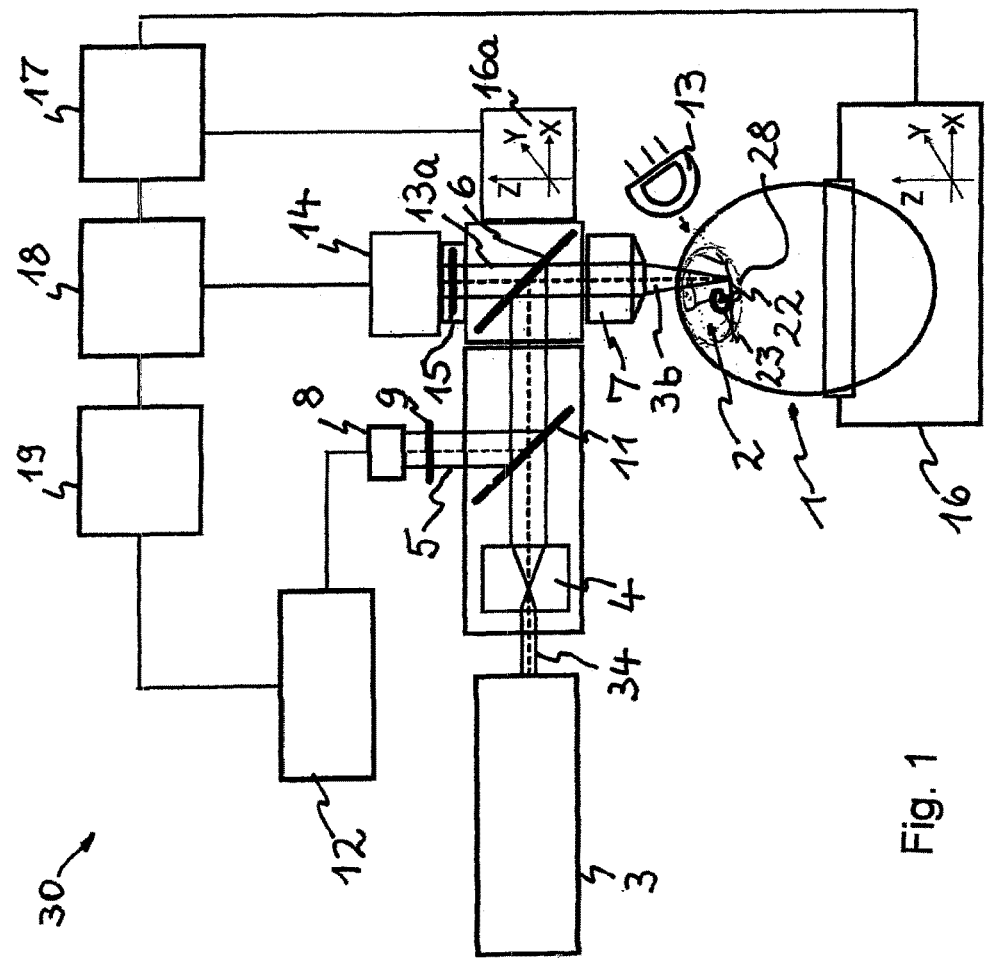

In FIG. 1, a schematic illustration of a first device 30 for the optical in ovo sex determination of a fertilized and incubated bird egg 1 based on generated fluorescence radiation 5 is shown, wherein the device 30 comprises an egg-mounting unit 16, on which the egg 1 is mounted;
a position-evaluation device 17 which is connected to the egg-mounting unit 16;
a radiation device 13 with light in the visible wavelength range for irradiating at least one extra-embryonic blood vessel 22, one embryonic blood vessel 24, or the heart 25 of the embryo 23;
  a detector (for example, a camera) 14 for visible or green light 13a for the detection of at least one extra-embryonic blood vessel 22, one embryonic blood vessel 24, or the heart 25 of the embryo 23, wherein the detector 14 is connected to the positioning evaluation device 18;
a device 6 for introducing laser light 34 into the egg 1, which device 6 is at least connected to
a laser source 3 emitting laser light 34;
a detector 8 for recording the fluorescence radiation 5;
a control unit 17 for XYZ-positioning of the device 6 onto the hole 2 created in the egg 1;
a sex-determination evaluation unit 19 that is connected to the amplification and detection unit 12 and to the positioning evaluation unit 18, which is connected to the control unit 17.

In FIG. 1, a device 11 according to the invention for separating the fluorescence radiation 5 from the backscatter radiation is arranged between a collimator 4 for collimating the laser beam 34 and the device for introducing the laser beam 34 into the egg 1, wherein between the beam-separating device 11 and at least one fluorescence detector 8 respectively one beam path-specific detection filter 9 for the transmission of the fluorescence radiation 5 is integrated.

The detection filter 9 can be an adapted, predefined bandpass filter.

The following can take place in the sex-determination evaluation unit 19:

an evaluation of the backscatter radiation 5, 50, 51, 52, including the fluorescence radiation 5, 51, 52, from the recorded spectral intensity of the fluorescence radiation 51, 52 in a spectral range redshifted to the excitation wavelength, wherein the sex-specific properties of the male blood and the female blood are contained in the intensity and in the spectral profile of the recorded fluorescence radiation 51, 52, and wherein at least one of the intensity levels determined from the measured spectral intensities of the fluorescence radiation 51, 52, or the values assigned thereto, for the male blood has an evaluable value distinct from at least one of the determined intensity levels, or the values assigned thereto, for the female blood in the blood vessels 22, 24, 25; and therefore a determination of the sex of the bird egg 1 from the difference of at least one of the values of the fluorescence intensity levels 51, 52, or the values assigned thereto, or from a comparison with a threshold value TV with programming means and/or optional logical operations present in the evaluation unit 19 can occur.

The light in the visible wavelength range, with which the radiation device 13 is provided in order to irradiate at least one blood vessel 22, 24 or the heart 25, can preferably be green light.

The laser beam that is produced in the laser 3 can be transmitted by means of mirrors or by means of fiber optics. The laser beam 34 is collimated using the collimator 4.

The laser beam 34 is transmitted to the egg and, using a lens 7, focused onto an extra-embryonic blood vessel 22, an embryonic blood vessel 24, or the heart 25 of the embryo 23.

The fluorescence radiation 5 generated is collected using the same lens 7.

A beam splitter 6 is used to separate the fluorescent signal 5 from the visible light 13a of the radiation source 13.

The light in the visible spectral range 13a is transmitted to the camera 14; a filter 15 removes remaining beams of the laser light.

A beam splitter 11 is used to separate the fluorescence radiation 5 that strikes the detector 8. The detector 8, typically a photodiode or an avalanche photodiode or a photomultiplier, measures the intensity of the fluorescence radiation.

The bandpass filter 9 selects the spectral range to be measured for the fluorescence.

A detection unit 12 amplifies, filters, and measures the signal from the detector, which signal is sent from the detection unit 12 to the sex-determination evaluation unit 19.

The measured intensity can be compared with a measured threshold value in the evaluation unit 19, and the sex of the egg is thus determined.

FIG. 1a shows an enlargement of the hole 2 from FIG. 1. Present therein are extra-embryonic blood vessels 22, embryonic blood vessels 24, and the embryo 23 with the heart 25 located therein.

Figure 5A:
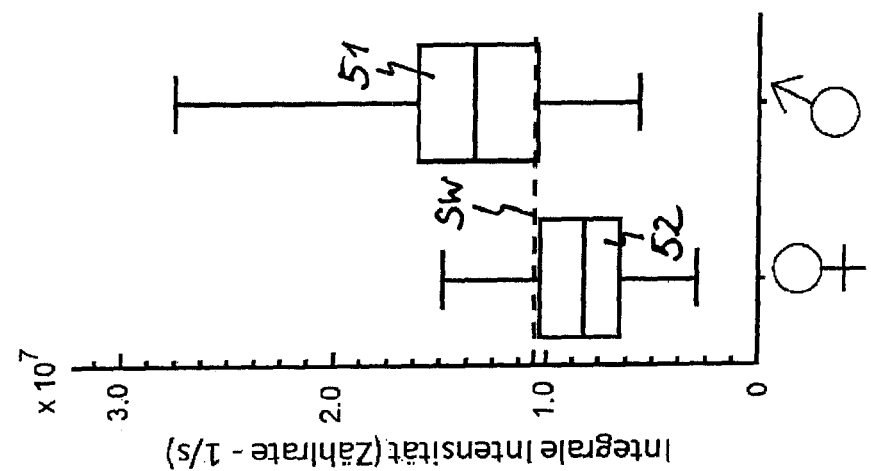
FIG. 5a shows the integral intensities from FIG. 5 for the entire spectral range.
Figure 5:
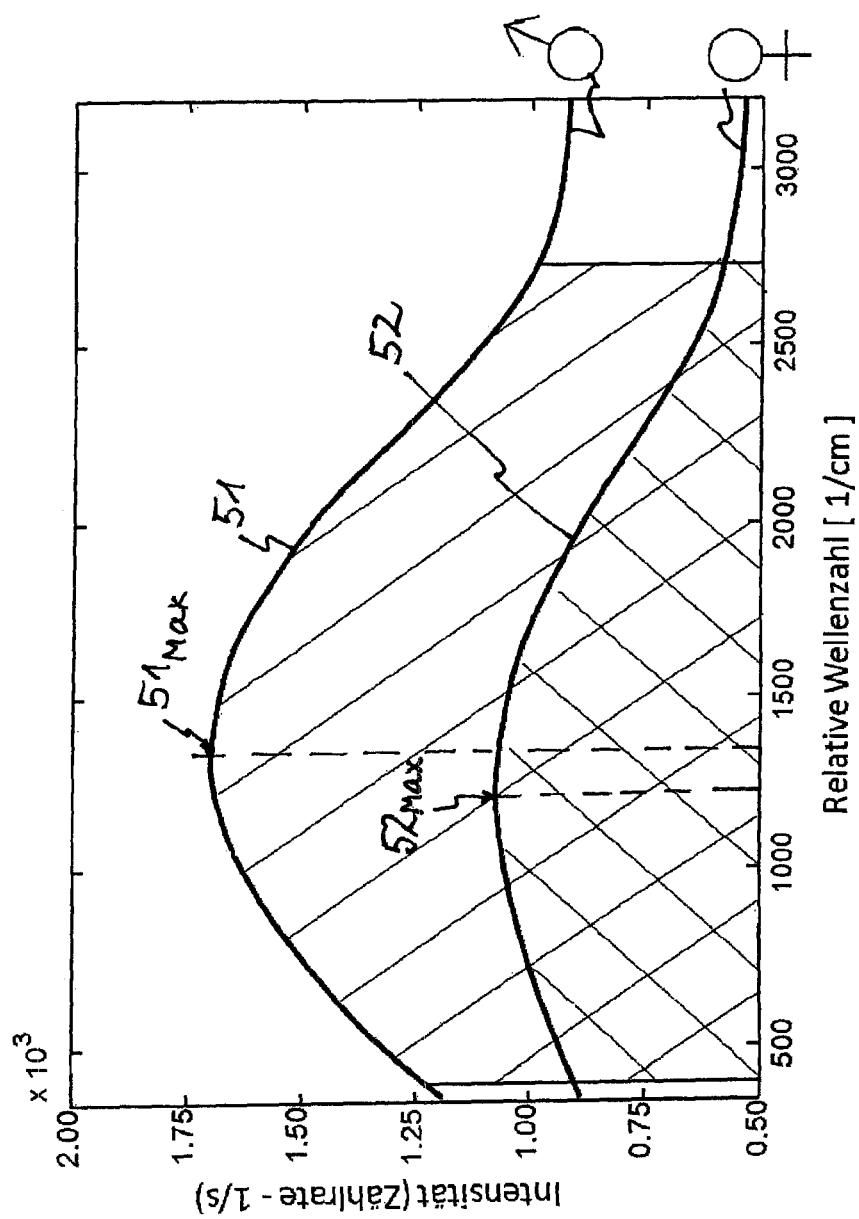

The recorded spectral radiation related to the first device 30 and shown in FIG. 5 is variable within the spectral range, but is always redshifted in comparison to the excitation wavelength of the laser 3. Typically, a frequency shift is between 100 cm$^{-1}$ and 4000 cm$^{-1}$. In the redshifted spectral range indicated in FIG. 5, the autofluorescence of the blood is different for male embryos and for female embryos. The autofluorescence of the male blood has a higher intensity curve 51 than the intensity curve 52 for the female blood, and the spectral fluorescence maximum 51$_{Max}$ of the male blood is slightly shifted to higher wavenumbers compared to the fluorescence maximum 52$_{Max}$ of the female blood.

In FIG. 5, the fluorescence intensity/frequency number curves for the first device 30 according to the invention from FIG. 1 for determining the sex of incubated birds' eggs based on generated fluorescence radiation after excitation by means of a measurement of the integral intensity, as is shown in FIG. 5a, is shown (each with different shading lines).

Figure 5C:
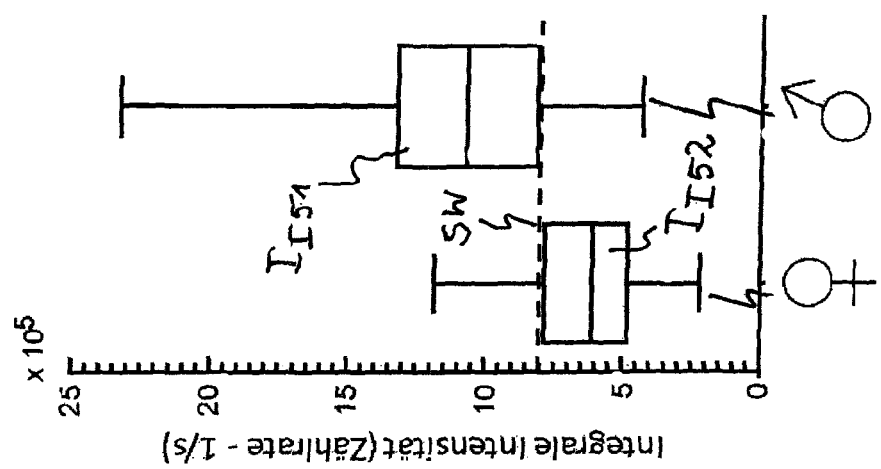
FIG. 5c shows the integral intensities related to FIG. 5b.
Figure 5B:
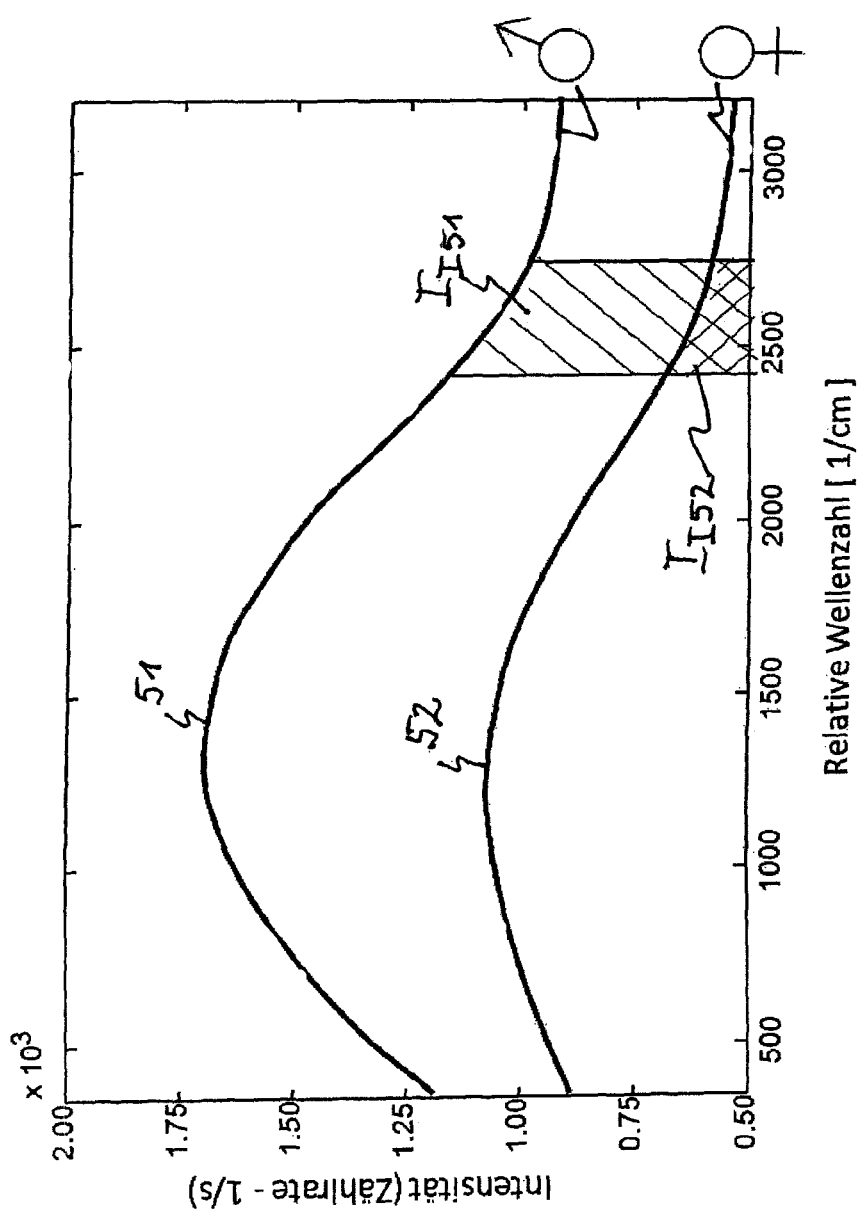
FIG. 5b shows the spectral intensity curve for a predefined partial spectral range.

In the evaluation unit 19, at least the intensity levels determined for a predefined spectral range between approx. 2400 and 2750 cm$^{-1}$ from the established fluorescence intensity/wavenumber curves 51, 52 can, according to FIGS. 5, 5b and 5c, be defined as the integral intensity $I_{I51}$ of the fluorescence radiation 51 of the male blood and as the integral intensity $I_{I52}$ of the fluorescence radiation 52 of the female blood according to FIG. 5c in order to determine the sex.

The following are carried out in configuration 1 according to FIG. 1:

The excitation takes place at one wavelength from one laser 3.

The entire spectral range or a spectral sub-range of the fluorescence radiation and backscatter radiation is recorded with a detector/sensor 8 and with a predefined bandpass filter 9.

The signal is possibly amplified.

For the recorded and possibly amplified intensity, an adapted threshold value TV is defined in order to distinguish between female embryos and male embryos. The blood of female embryos is characterized by an intensity value $I_{I52}$ that is smaller than the adapted threshold value TV; the blood of male embryos is characterized by an intensity value $I_{I51}$ that is larger than the adapted threshold value TV.

Furthermore, according to FIG. 5, the intensity levels determined for a predefined spectral range from the established fluorescence intensity/wavenumber curves 51, 52 can be defined in the evaluation unit 19 as the intensity maximum 51$_{Max}$ of the fluorescence radiation 51 of the male blood and as the intensity maximum 52$_{Max}$ of the fluorescence radiation 52 of the female blood in order to determine the sex.

In FIG. 2, which corresponds to configuration 2, a second device 31 for the in ovo sex determination of a fertilized and incubated bird egg 1 based on detected fluorescence radiation 5 is shown in a schematic illustration, wherein the device 31 comprises an egg-mounting unit 16, on which the egg 1 is mounted;
a position-evaluation device 17 which is connected to the egg-mounting unit 16;
a radiation device 13 with light in the visible wavelength range, preferably in the green wavelength range, for irradiating at least one blood-carrying vessel, such as an extra-embryonic blood vessel 22, an embryonic blood vessel 24, or the heart 25 of the embryo 23;
a detector (for example, a camera) 14 for visible or green light 13a for the detection of at least one extra-embryonic blood vessel 22, one embryonic blood vessel 24, or the heart 25 of the embryo 23, wherein the detector 14 is connected to the positioning evaluation device 18;
a device 6 for introducing laser light 34 into the egg 1, which device 6 is at least connected to
  a laser source 3 emitting laser light 34; and
  two or more/in FIG. 2 five and in FIG. 6 accordingly eight presented detectors 8 for recording the fluorescence radiation 5 in two or more spectral regions D1 to D8 which are selected by means of predefined/in FIG. 2 five and in FIG. 6 accordingly eight (only five are drawn) presented bandpass filters; and
a control unit 17 for XYZ-positioning of the device 6 onto the hole 2 created in the egg 1;
a sex-determination evaluation unit 19 that is connected to the amplification and detection unit 12 and to the positioning evaluation unit 18, which is connected to the control unit 17.

The following are carried out in configuration 2 according to FIG. 2:

The excitation takes place at one wavelength (laser source 3).

The entire spectral range or a spectral sub-range of the fluorescence and backscatter is recorded with more than one detector/sensor 8 and predefined bandpass filters 9 that select different spectral ranges D1 to D8.

The signal is possibly amplified.

To obtain the sex of the embryo 23, the recorded and possibly amplified signal intensities are fed to a mathematical evaluation. The mathematical evaluation can be based on the evaluation of intensities, intensity ratios, intensity sums or differences, and can also utilize supervised classification methods such as discriminant analysis, support vector machines, or neural networks. The recorded signal intensities can be evaluated without data processing, or can be normalized before the evaluation, for example, by means of vector normalization or area normalization.

For this purpose, the intensity levels $I_{D1}$ to $I_{D8}$ determined for the eight predefined spectral ranges D1 to D8 from the established fluorescence intensity/wavenumber curves 51, 52 can, according to FIG. 6, be defined in the evaluation unit 19 as integral intensities of the fluorescence radiation 51 of the male blood and as integral intensities of the fluorescence radiation 52 of the female blood, at which radiation, for example, the difference between the respective integral intensities is the greatest, in order to determine the sex.

The laser beam illustrated in FIG. 2, which is produced in the laser 3, can be transmitted by means of mirrors or by means of fiber optics. The laser beam 34 is collimated using the collimator 4.

The laser beam 34 is transmitted to the egg and, using a lens or an objective lens 7, focused onto an extra-embryonic blood vessel 22, an embryonic blood vessel 24, or the heart 25 of the embryo 23.

The fluorescence radiation 5 is collected with the same lens/objective lens 7.

A beam splitter 6 is used to separate the fluorescent signal 5 from the visible light 13*a* of the radiation source 13.

The light in the visible spectral range 13*a* is transmitted to the camera 14; a filter 15 removes remaining beams of the laser light.

The beam splitter 11 is used as a device for separating the fluorescence radiation, in order to separate the fluorescence radiation 5 that strikes the detector 8. A detector 8, typically a photodiode or an avalanche photodiode or a photomultiplier, measures the intensity of the fluorescence radiation.

The eight (only five are drawn) bandpass filters 9 presented according to FIG. 6 select the spectral ranges D1 to D8 of the fluorescence, which are recorded using each of the eight presented (only five are drawn) detectors 8.

A detection unit 12 amplifies, filters, and measures the signal from the detector 8, which signal is sent to the sex-determination evaluation unit 19.

In order to determine the sex, the signal intensities are evaluated in the evaluation unit 19 using one of the following methods or a combination of the following methods:
intensities are compared with threshold values;
intensity ratios are compared with threshold values;
intensity sums or differences are compared with threshold values;
supervised classification methods, such as discriminant analyses, support vector machines, or neural networks, for example, are applied to the intensity values.

The signal intensities $I_{D1}$ to $I_{D8}$ can be normalized, as is shown in FIG. 6*b*, for example with vector normalization or area normalization, and can then be mathematically evaluated with one of the following methods or a combination of the following methods, in order to obtain the sex:
normalized intensities in FIG. 6*b* are compared to threshold values, for example;
ratios between normalized intensities are compared to threshold values;
sums or differences of normalized intensities are compared to threshold values;
supervised classification methods, such as discriminant analyses, support vector machines, or neural networks, for example, are applied to the normalized intensity values.

In FIG. 3, which corresponds to configuration 3, a third device 32 for the in ovo sex determination of a fertilized and incubated bird egg 1 based on detected fluorescence radiation is shown in a schematic illustration, wherein the device 32 comprises
an egg-mounting unit 16, on which the egg 1 is mounted;
a position-evaluation device 17 which is connected to the egg-mounting unit 16;
a radiation device 13 with light in the visible or green wavelength range for irradiating at least one extra-embryonic blood vessel 22, one embryonic blood vessel 24, or the heart 25 of the embryo 23;
a detector (for example, a camera) 14 for visible or green light 13*a* for the detection of at least one extra-embryonic blood vessel 22, one embryonic blood vessel 24, or the heart 25 of the embryo 23, wherein the detector 14 is connected to the positioning evaluation device 18;
a device 6 for introducing laser light 34 into the egg 1, which device 6 is at least connected to
two or more laser beam sources 35, 36 emitting laser light 34;
two or more collimators 41, 42, one for each laser beam source 35, 36;
at least one or more beam couplers 26 or mirrors/semi-permeable mirrors 10 for the laser beam source 35, 36;
two or more detectors 8 for recording the fluorescence radiation 5 in two or more spectral ranges that are selected by means of bandpass filters 9;
a control unit 17 for XYZ-positioning of the device 6 onto the hole 2 created in the egg 1;
a sex-determination evaluation unit 19 that is connected to the amplification and detection unit 12 and to the positioning evaluation unit 18, which is connected to the control unit 17.

The following are carried out in configuration 3 according to FIG. 3:
The excitation takes place at two or more wavelengths. The excitation radiation is produced by two or more lasers 35, 36.
The entire spectral range or a spectral sub-range of the fluorescence, which range or sub-range is generated by each excitation wavelength, is recorded with two or more detectors/sensors 8 and predefined bandpass filters 9.
The recorded and possibly amplified signal intensities I are mathematically evaluated in order to obtain the sex. The mathematical evaluation can be based on the evaluation of intensities, intensity ratios, intensity sums or differences, and can also utilize supervised classification methods such as discriminant analysis, support vector machines, or neural networks.

According to FIG. 7, if at least two laser beam sources 35, 36 are used, the intensity levels determined from multiple measured fluorescence intensity/wavenumber curves 51, 52 for a predefined spectral range between approx. 500 cm$^{-1}$ and approx. 3500 cm$^{-1}$ can be defined in the evaluation unit 19 as the integral intensities $I_{I511}$, $I_{I512}$ of the fluorescence radiation 51 of the male blood and as the integral intensities $I_{I521}$, $I_{I522}$ of the fluorescence radiation 52 of the female blood as a function of the wavelengths emitted from the laser beam sources 35, 36.

In this manner, the certainty for the rapid determination of the sex from the simultaneous fluorescence radiation measurements of the respective blood is to be increased.

Finally, if at least one laser beam source 3 is used or multiple laser beam sources 35, 36 are used, the intensity levels determined from multiple established fluorescence intensity/wavenumber curves 51, 52 for a predefined spectral range can be respectively defined in the evaluation unit 19 for the male blood and for the female blood in a combined manner, for example, by means of a logical operation in the evaluation unit 19, for evaluation and for the rapid determination of the sex of the birds' eggs 1.

The laser beams 34 that are produced in the lasers 35, 36 can be transmitted by means of mirrors or by means of fiber optics. The laser beams 34 are collimated using the collimators 41, 42.

The laser beams 34 are overlapped using a beam coupler 26.

The laser beams 34 are transmitted to the egg 1 and, using a lens or an objective lens 7, focused onto an extra-embryonic blood vessel 22, an embryonic blood vessel 24, or the heart 25 of the embryo 23.

The fluorescence radiation 5 is collected with the same lens/objective lens 7 that produces the laser focus.

A beam splitter 6 is used to separate the fluorescent signal 5 from the visible light 13*a* of the radiation source 13.

The light in the visible spectral range 13*a* is transmitted to the camera 14; a filter 15 removes remaining beams of the laser light.

A beam splitter 11 is used to separate the fluorescence radiation 5 that strikes the detectors 8. The detectors 8, typically each a photodiode or an avalanche photodiode or a photomultiplier, measure the intensities of the fluorescence radiation 5.

Two or more predefined bandpass filters 9 select the spectral ranges of the fluorescence radiation, which ranges are recorded with each of the detectors 8.

A detection unit 12 amplifies, filters, and measures the signals from the detectors 8, which signals are sent to the sex-determination evaluation unit 19.

In order to determine the sex, the signal intensities $I_{I511}$, $I_{I512}$, $I_{I521}$, $I_{I522}$ can be evaluated using one of the following methods or a combination of the following methods:
  intensities are compared with threshold values;
  intensity ratios are compared with threshold values;
  intensity sums or differences are compared with threshold values;
  supervised classification methods, such as discriminant analyses, support vector machines, or neural networks, for example, are applied to the intensity values.

The signal intensities can also be normalized in this case, for example, with vector normalization or area normalization, and can then be mathematically evaluated with one of the following methods or a combination of the following methods, in order to obtain the sex:
  normalized intensities are compared to threshold values;
  ratios between normalized intensities are compared with threshold values;
  sums or differences of normalized intensities are compared with threshold values;
  supervised classification methods, such as discriminant analyses, support vector machines, or neural networks, for example, are applied to the normalized intensity values.

SVM—supporting vector machine, LDA—linear discriminant analysis, KNN—nearest neighbor classification or the ANN—artificial neural networks method can be used as classification methods. Other methods, such as non-linear processes/methods or supervising devices or SIMCA, for example, can also be used. The algorithms classify the intensity values,
  wherein for this purpose a reference intensity set with "male" reference intensities and "female" reference intensities having a known sexual correlation is required. The algorithm compares the reference intensity set with other reference intensity sets of the sex class and examines the similarity of the new reference intensity set to the known stored reference intensity sets.
  A step for outputting the results of the determination of the respective sex of the birds' eggs, wherein the egg 1 is separated out if the minimum certainty for "male" of equal to or less than 45% is reached. Otherwise a female egg 1 is present which will continue to be incubated.

In the related FIG. 7, fluorescence intensity/wavenumber curves are shown for the third device according to the invention from FIG. 3 for determining the sex of incubated birds' eggs 1 based on generated fluorescence radiation 5 after excitation by means of two laser beam sources 35, 36 emitting different wavelengths with a measurement of the different intensity curves 51, 52 (solid and dashed, respectively).

In FIG. 4, which corresponds to configuration 4, a fourth device 33 for the in ovo sex determination of a fertilized and incubated bird egg 1 based on backscatter radiation, including the fluorescence radiation 5, is shown in a schematic illustration, wherein the device 33 comprises an egg-mounting unit 16, on which the egg 1 is mounted;
a position-evaluation device 17 which is connected to the egg-mounting unit 16;
a radiation device 13 with light in the visible or green wavelength range for irradiating at least one extra-embryonic blood vessel 22, one embryonic blood vessel 24, or the heart 25 of the embryo 23;
a detector (for example, a camera) 14 for visible or green light 13a for the detection of at least one extra-embryonic blood vessel 22, one embryonic blood vessel 24, or the heart 25 of the embryo 23, wherein the detector 14 is connected to the positioning evaluation device 18;
a device 6 for introducing laser light 34 into the egg 1, which device 6 is at least connected to
a laser source 3 emitting laser light 34;
a control unit 17 for XYZ-positioning of the device 6 onto the hole 2 created in the egg 1;
a spectrometer 20 for recording the fluorescence radiation 5 and the overlapping Raman scattered radiation, wherein a notch filter/shortpass filter 21 is arranged in front of the spectrometer 20; and
a sex-determination evaluation unit 19 that is connected to the detection unit 12 and to the positioning evaluation unit 18, which is connected to the control unit 17.

The devices 30, 31, 32, 33 according the invention essentially differ in regard to the components and parts used to separate the backscatter radiation, including the fluorescence radiation 5 and also the Raman scattered radiation 50, in particular also in regard to the number of bandpass filters 8, the number of detectors 8, and the evaluation unit 19, depending on which spectral intensity or assigned value, particularly of the fluorescence radiation 5, is evaluated in the evaluation unit 19 and which programming means are contained in the evaluation unit 19 for the envisaged sex determination.

The following are carried out in configuration 4 according to FIG. 4 with the recording of the fluorescence radiation 5, 51, 52 and the Raman scattered radiation 50:

The excitation takes place at one wavelength (laser 3).
The entire spectral range or a spectral sub-range of the fluorescence and backscatter is recorded and fed to a spectrometer 20.
The sex information is extracted from the recorded spectrum, which is composed of an overlapping of fluorescence and inelastic Raman backscatter. The recorded spectrum in the spectral range of approximately 100 $cm^{-1}$ to 4000 $cm^{-1}$ or a spectral sub-range thereof is evaluated directly, or a normalization of the data is carried out. Supervised classification methods, such as discriminant analysis, support vector machines, or neural networks, are then applied in order to obtain the sex information.
If the likewise generated and recorded Raman scattered radiation is taken into consideration, the intensity levels determined for a predefined spectral range from the measured fluorescence intensity/wavenumber curves 51, 52 can, according to FIG. 8, be defined in the evaluation unit 19 as the integral intensity $I_{I51}$ of the fluorescence radiation 51 of the male blood and as the integral intensity $I_{I52}$ of the fluorescence radiation 52 of the female blood and the Raman scattered radiation $50_{51}$, $50_{52}$ respectively overlapping the fluorescence radiation 51, 52 can be defined for the evaluation in order to rapidly determine the sex of the egg's blood.

The rectangle 53 drawn in FIG. 8 represents the selected spectral range that is used in the stated classification example.

For this purpose, fluorescent intensity/wavenumber curves for the fourth device 33 according to the invention for determining the sex of incubated birds' eggs 1 based on generated fluorescence radiation 5 and inelastic Raman scattered radiation 50 after excitation by means of a laser beam source 3 for the measurement of the two overlapping intensities 51 and 50, 52 and 50 are shown in the related FIG. 8.

The recorded spectral inelastic backscatter radiation related to the fourth device 33 and shown in FIG. 8 is variable within the spectral range, but is always redshifted in comparison to the excitation wavelength of the laser 3. Typically, a wavenumber shift is between approx. 500 $cm^{-1}$ and 3500 $cm^{-1}$. In the spectral range 53 indicated (rectangle), the autofluorescence of the blood is different for male embryos and for female embryos. The autofluorescence of the male blood has a higher intensity curve 51 than the intensity curve 52 for the female blood.

The clearly weaker Raman scattered radiation $50_{51}$, $50_{52}$ of the male embryos and female embryos is overlaid onto the fluorescence radiation 51, 52, respectively.

The spectroscopic evaluation takes place in the evaluation unit 19 involving mathematic classification algorithms.

For performing the spectral classification and outputting the results thereof, a multi-stage process is specified:
1. A measuring step for the spectra of the egg 1 being analyzed;
2. A data preprocessing step with
    a reduction of the spectral range of the reflection to a spectral range between 500 $cm^{-1}$ and 4000 $cm^{-1}$ or less;
    a normalizing of the spectra to an integral intensity by means of area or vector normalization, which can possibly be performed, but is not absolutely necessary.
3. A spectral classification step with
the application of a supervised classification. SVM—supporting vector machine, LDA—linear discriminant analysis, KNN—nearest neighbor classification or the ANN—artificial neural networks method can be used as classification methods. Other methods, such as non-linear processes/methods or supervising devices or SIMCA, for example, can also be used. LDA classifies multiple spectral ranges, that is, the intensity values of these ranges,
possibly with a verification step, wherein for this purpose a set of reference spectra with "male" reference spectra and "female" reference spectra having a known sexual correlation is required. The algorithm compares the spectrum with other spectra of the sex class and examines the similarity of the new spectrum to the known stored reference spectra.

After the step for outputting and displaying the results for determining the respective sex of the birds' eggs, the egg 1 is then separated out if the minimum certainty for "male" of equal to or less than 45% is reached. Otherwise a female egg 1 is present which will continue to be incubated.

In FIG. 8a, the normalized intensities of both forms of fluorescence radiation 51, 52 are illustrated. As a result of the normalization, it becomes evident that, compared to the spectra of the female blood, the spectra of the male blood exhibit a different spectral profile.

Implemented exemplary embodiments and the results are explained below in detail:

A 15 mm opening was created at the pointed end of 165 chicken eggs at day 3.5 of incubation. The reference sex of the eggs 1 was obtained by means of a subsequent PCR determination. The PCR determination revealed that 80 eggs contained a male embryo and 85 eggs contained a female embryo. An extra-embryonic blood vessel 22 was selected under green LED illumination (500 nm-550 nm) and by means of a camera 14 with significant enlargement.

A CW laser beam of the laser beam source 3 (output: 200 mW; excitation wavelength: 785 nm) was focused onto an extra-embryonic blood vessel 22 using an objective lens 7 (numerical aperture NA=0.4).

The aforementioned devices 30, 31, 32, 33 operate at least according to one of the methods indicated below:

In the method according to the invention for the optical in ovo sex determination of fertilized and incubated birds' eggs, the following steps are carried out:
   monitoring the chronological progression of the incubation until at least one identifiable blood vessel 22, 24 or the heart 25 develops with flowing blood;
   creating a hole 2 in the shell 28 of the bird egg 1 by means of a hole-creating unit;
   finding the blood vessels 22, 24 developing in the egg 1, or finding the heart 25, using a vision system 13, 13a and a coaxial or lateral illumination with light in the visible wavelength range;
   positioning at least one blood vessel 22, 24 or the heart 25 in the laser focus of at least one laser beam source 3; 35, 36, either by moving the egg 1 or by moving an objective lens 7 that produces the laser focus;
   irradiating the blood vessel 22, 24 or the heart 25 with at least one laser beam source 3, 35, 36 emitting an excitation wavelength;
   recording the backscatter radiation 5, 50, 51, 52 of the irradiated blood vessel 22, 24 or the heart 25 using at least one detector 8 that is connected to at least one evaluation unit 19 connected to a downstream amplification and detector unit 12, wherein in the case of a movement of the selected blood vessel 22, 24 or the heart 25 out of the laser beam 3b, a tracking of the blood vessels 22, 24 or the heart 25 or the objective lens/lens 7 producing the laser focus can take place during the recording.

The following steps are then carried out according to the invention:
   evaluation of the backscatter radiation 5, 50, 51, 52, including the fluorescence radiation 5, 51, 52, in the evaluation unit 19 from the recorded spectral intensity of the fluorescence radiation 51, 52 in a spectral range redshifted to the excitation wavelength, wherein the sex-specific properties of the male blood and the female blood are contained in the intensity and in the spectral profile of the recorded fluorescence radiation 51, 52, and wherein at least one of the intensity levels determined from the measured spectral intensities of the fluorescence radiation 51, 52, or the values assigned thereto, for the male blood has an evaluable value distinct from at least one of the determined intensity levels, or the values assigned thereto, for the female blood in the blood vessels 22, 24 or in the heart 25;
   determination of the sex of the bird egg 1 from the difference of at least one of the values of the fluorescence intensity levels 51, 52, or the values assigned thereto, in the evaluation unit 19; and subsequently at least
   one display of the sex determined in the evaluation unit (19) for the embryo (23) in the bird egg (1).

The light in the visible wavelength range, with which the radiation device 13 of the vision system is provided in order to irradiate at least one blood vessel 22, 24 or the heart 25, can preferably be green light.

The respectively evaluable distinct value for the intensity levels can at least be based on a predefined limit value/ threshold value that is stored in the evaluation unit 19 and assigned to the intensity level.

In the evaluation unit 19, the intensity levels determined for a predefined spectral range from the established fluorescence intensity/wavenumber curves 51, 52 can be defined as the integral intensity $I_{I51}$ of the fluorescence radiation 51 of the male blood and as the integral intensity $I_{I52}$ of the fluorescence radiation 52 of the female blood.

In the evaluation unit 19, the intensity levels determined for a predefined spectral range from the established fluorescence intensity/wavenumber curves 51, 52 can also be defined as the intensity maximum $51_{Max}$ of the fluorescence radiation 51 of the male blood and as the intensity maximum $52_{Max}$ of the fluorescence radiation 52 of the female blood.

Furthermore, the intensity levels $I_{D1}$ to $I_{D8}$ determined for predefined and adjacently ordered spectral ranges from the established fluorescent intensity/number curves 51, 52 can be defined in the evaluation unit 19 as the integral intensity of the fluorescence radiation 51 of the male blood and as the integral intensity of the fluorescence radiation 52 of the female blood within the predefined spectral ranges, at which radiation, for example, the differences between the respective intensity levels $I_{D151}$ to $I_{D852}$ is the greatest.

In the evaluation unit 19, if one laser beam source 3 is used, the intensity levels determined for a predefined spectral range from the established fluorescence intensity/wavenumber curve 51, 52 can be respectively defined for the male blood and for the female blood such that they are combined by means of a logical operation for evaluation.

In the evaluation unit 19, if at least two laser beam sources 35, 36 are used, the intensity levels determined for a predefined spectral range from multiple established fluorescence intensity/wavenumber curves 51, 52 can thereby be defined as the integral intensities $I_{I511}$, $I_{I512}$ of the fluorescence radiation 51 of the male blood and as the integral intensities $I_{I521}$, $I_{I522}$ of the fluorescence radiation 52 of the female blood.

In the evaluation unit 19, if at least two laser beam sources 35, 36 are used, the intensity levels determined for a predefined spectral range from multiple established fluorescence intensity/wavenumber curves 51, 52 can be respectively defined for the male blood and for the female blood such that they are combined for evaluation.

In the evaluation unit 19, the intensity levels determined for a predefined spectral range from the established fluorescence intensity/wavenumber curves 51, 52 can be defined as the integral intensity $I_{I51}$ of the fluorescence radiation 51 of the male blood and as the integral intensity $I_{I52}$ of the fluorescence radiation 52 of the female blood and the Raman scattered radiation $50_{51}$, $50_{52}$ respectively overlapping the fluorescence radiation 51, 52 can be defined for the evaluation alone or in combination with the other defined intensity levels and assigned values, wherein if the intensity levels and assigned values are combined, the Raman scattered radiation and the fluorescence radiation are evaluated together by means of a logical operation and/or at the hardware level by means of logical elements.

The evaluation unit (19) can comprise, for the logical linking of intensity levels and assigned values or values derived from the intensity levels, programming means for performing at least one logical operation and/or can comprise logical elements (AND and others) embodied as hardware for performing at least one logical operation.

If a pulsed laser beam from the laser beam source 3 is used, the fluorescence intensity generated can be measured in a time-resolved manner and, from the time constant τ of the decay curve of the time-resolved fluorescence intensity, a sex determination can be carried out, wherein a different time constant $\tau_{male}$, $\tau_{female}$, with $\tau_{male} \neq \tau_{female}$, is respectively determined for male blood and for female blood in order to determine the sex.

Lastly, examples (ex.) of the certainty of identifying the sex are provided below:

EVALUATION EX. 1

The fluorescence intensity 51, 52 (5) was recorded in the range between 807 nm and 1000 nm (corresponds to a frequency shift in the range between 350 cm$^{-1}$ and 2750 cm$^{-1}$), as is shown in FIG. 5.

The adapted threshold value TV for the intensity at which the sexes can be separated was found at 1.06*10^7 counts/s on the detector 8. 70% of the male embryos had an intensity above the adapted threshold value TV, and 81% of the female embryos had an intensity below the adapted threshold value TV, as is shown in FIG. 5a.

EVALUATION EX. 2

The recorded fluorescence range was limited to a range of 970 nm to 1000 nm (corresponds to a frequency shift in the range of 2430 cm$^{-1}$ to 2750 cm$^{-1}$) according to FIG. 5b and FIG. 5c.

The threshold value TV for the intensity at which the sexes can be separated was found at 8.25*10^5 counts/s on the detector 8. 73% of the male embryos had an intensity above this threshold value TV, and 84% of the female embryos had an intensity below this threshold value TV according to FIG. 5c.

EVALUATION EX. 3

The fluorescence radiation 5 was, as is shown in FIG. 6, recorded in eight separate spectral ranges D1, D2, D3, D4, D5, D6, D7, D8, each with a width of 300 cm$^{-1}$, in the range between 350 cm$^{-1}$ and 2750 cm$^{-1}$. The recorded intensities according to FIG. 6a were fed to a linear discriminant analysis. 75% of the male embryos and 95% of the female embryos were classified correctly.

EVALUATION EX. 4

The fluorescence radiation 5, 51, 52 was, as is shown in FIG. 6 and FIG. 6a, recorded in eight separate spectral ranges D1, D2, D3, D4, D5, D6, D7, D8, each with a width of 300 cm$^{-1}$, in the frequency range between 350 cm$^{-1}$ and 2750 cm$^{-1}$. The recorded intensities were vector-normalized and fed to a discriminant analysis, as is shown in FIG. 6b. 86% of the male embryos and 91% of the female embryos were classified correctly.

EVALUATION EX. 5

The fluorescence radiation 5, 51, 52 and the Raman scattered radiation 50 were recorded and sent to a spectrometer 20. The spectra in the spectral range of 600 cm$^{-1}$ to 1500 cm$^{-1}$ (rectangle 53) were fed to a linear discriminant analysis according to FIG. 8. 94% of the male embryos and 88% of the female embryos were classified correctly.

EVALUATION EX. 6

The fluorescence radiation 5, 51, 52 according to FIG. 8 and the Raman scattered radiation 50 were recorded and sent to a spectrometer 20. The spectra in the spectral range of 600 cm$^{-1}$ to 1500 cm$^{-1}$ were normalized according to FIG. 8a and fed to a linear discriminant analysis. 85% of the male embryos and 80% of the female embryos were classified correctly.

The advantages of the sex determination according to the invention are:
no impairment of hatching and the subsequent development of the chick, and
a performance of the sex determination in a highly accurate manner in real time, at a very early point and with the aid of non-contact determination without sampling.

LIST OF REFERENCE CHARACTERS

| | |
|---|---|
| 1 | Egg |
| 2 | Hole in the eggshell 28 |
| 3 | Laser beam source |
| 3b | Laser light introduced into the hole 2 in the shell 28 |
| 4 | Collimator |
| 5 | Radiation for detection/fluorescence radiation |
| 6 | Device for introducing laser radiation into the egg (beam splitter) |
| 7 | Lens/objective lens for focusing the laser radiation and collecting the fluorescence radiation |
| 8 | Detector(s) |
| 9 | Detection filter(s)/bandpass filter(s) |
| 10 | Detection beam splitter/mirror |
| 11 | Device for separating the fluorescence (beam splitter) |
| 12 | Amplification and detection unit |
| 13 | Light source/radiation device of the vision system VIS |
| 13a | Transmitted or scattered visible light |
| 14 | Detector/camera for the detection of light 13a |
| 15 | Camera filter |
| 16 | XYZ-positioning unit for egg position control |
| 16a | XYZ-positioning unit for lens position control |
| 17 | Control unit |
| 18 | Positioning evaluation unit |
| 19 | Evaluation unit/sex-determination evaluation unit |
| 20 | Spectrometer |
| 21 | Notch filter/shortpass filter |
| 22 | Extra-embryonic blood vessel |
| 23 | Embryo |
| 24 | Embryonic blood vessel |
| 25 | Heart |
| 26 | Beam coupler |
| 28 | Shell |
| 30 | First device |
| 31 | Second device |
| 32 | Third device |
| 33 | Fourth device |
| 34 | Laser light |
| 35 | First laser beam source |
| 36 | Second laser beam source |
| 41 | First collimator |
| 42 | Second collimator |
| 50 | Raman scattered radiation |
| $50_{51}$ | Raman scattered radiation from the male blood |
| $50_{52}$ | Raman scattered radiation from the female blood |
| 51 | Fluorescence intensity curve for the male blood |
| 52 | Fluorescence intensity curve for the female blood |
| 53 | Rectangle |
| $I_{I51}, I_{I51}$ | Integral intensities |
| $I_{I511}, I_{I512}, I_{I521}, I_{I522}$ | Integral intensities |
| $51_{Max}, 52_{Max}$ | Intensity maxima of the fluorescence intensity curves |
| D1 ... D8 | Predefined partial spectral ranges |
| T | Time constants |
| ♂ | Male |
| ♀ | Female |

The invention claimed is:

1. A method for optical in ovo sex determination of fertilized and incubated birds' eggs comprising:
monitoring a chronological progression of incubation until at least one identifiable blood vessel or a heart develops with flowing blood;
creating a hole in a shell of the bird egg by a hole-creating unit;
finding blood vessels developing in the bird egg, or finding the heart, using a vision system and a coaxial or lateral illumination with light in a visible wavelength range;
positioning at least one blood vessel or the heart in a laser focus of at least one laser beam source, either by moving the egg or by moving an objective lens that produces the laser focus;
irradiating the at least one blood vessel or the heart with at least one laser beam source emitting an excitation wavelength;
recording backscatter radiation of the irradiated at least one blood vessel or heart using at least one detector that is connected to at least one evaluation unit connected to a downstream amplification and detector unit, wherein during the recording a movement of the at least one blood vessel or the heart out of the laser beam takes place by a tracking of the at least one blood vessel or the heart or the objective lens;
wherein:
evaluation of the backscatter radiation, including fluorescence radiation, in the evaluation unit from a recorded spectral intensity of the fluorescence radiation in a spectral range redshifted to an excitation wavelength, wherein the sex-specific properties of male blood and of female blood are contained in the recorded spectral intensity and in a spectral profile of the recorded fluorescence radiation, and wherein at least one intensity level determined from measured spectral intensities of the fluorescence radiation, or values assigned thereto, for the male blood has an evaluable value distinct from at least one determined intensity level, or the values assigned thereto, for the female blood in the blood vessels or in the heart;
determination of the sex of the bird egg from a difference of at least one of values of the fluorescence intensity levels, or the values assigned thereto, in the evaluation unit; and
subsequent display of the sex determined in the evaluation unit for an embryo in the bird egg.

2. The method according to claim 1,
wherein
green light is used as light in the visible wavelength range, with which light a radiation device of the vision system is provided in order to irradiate the at least one blood vessel (22, 24) or the heart.

3. The method according to claim 2,
wherein
if one laser beam source is used, the fluorescent intensity levels determined for a predefined spectral range from an established fluorescence intensity / wavenumber curve are respectively defined for the male blood and for the female blood such that they are combined by a logical operation for evaluation.

4. The method according to claim 1,
wherein
fluorescent intensities are evaluated in the evaluation unit using one of the following methods or a combination of the following methods, in order to determine the sex:
fluorescent intensities are compared with threshold values;

fluorescent intensities ratios are compared with threshold values;
fluorescent intensity sums or differences are compared with threshold values;
supervised classification methods, such as discriminant analyses, support vector machines, or neural networks, for example, are applied to the values of fluorescent intensity.

5. The method according to claim 2,
wherein,
if at least two laser beam sources are used, the fluorescent intensity levels determined for a predefined spectral range from multiple established fluorescence intensity / wavenumber curves are respectively defined in the evaluation unit for the male blood and for the female blood such that they are combined by a logical operation for evaluation.

6. The method according to claim 1,
wherein
fluorescence intensities are normalized, with vector normalization or area normalization, and are then mathematically evaluated in the evaluation unit with one of the following methods or a combination of the following methods, in order to obtain the sex:
normalized fluorescent intensities are compared with threshold values;
ratios between normalized fluorescent intensities are compared with threshold values;
sums or differences of normalized fluorescent intensities are compared with threshold values;
supervised classification methods, such as discriminant analyses, support vector machines, or neural networks, for example, are applied to values of the normalized fluorescent intensities.

7. The method according to claim 1,
wherein
a respectively evaluable distinct value for the fluorescent intensity levels is based at least on a measured threshold value or a predefined threshold value that is stored in the evaluation unit and assigned to the fluorescent intensity level.

8. The method according to claim 1,
wherein
the fluorescent intensity levels determined for a predefined spectral range from an established fluorescence intensity / wavenumber curves are defined in the evaluation unit as an integral intensity of the fluorescence radiation of the male blood and as an integral intensity of the fluorescence radiation of the female blood.

9. The method according to claim 1,
wherein
the fluorescent intensity levels determined for a predefined spectral range from an established fluorescence intensity / wavenumber curves are defined in the evaluation unit as an intensity maximum of the fluorescence radiation of the male blood and as an intensity maximum of the fluorescence radiation of the female blood.

10. The method according to claim 1,
wherein
the fluorescent intensity levels determined for multiple predefined and adjacently arranged spectral ranges from an established fluorescent intensity / number curves are defined in the evaluation unit as an integral intensity of the fluorescence radiation of the male blood and as an integral intensity of the fluorescence radiation of the female blood within the predefined spectral ranges.

11. The method according to claim 1,
wherein
if at least two laser beam sources are used, the fluorescent intensity levels determined for a predefined spectral range from multiple established fluorescence intensity / wavenumber curves are defined in the evaluation unit as integral intensities of the fluorescence radiation of the male blood and as integral intensities of the fluorescence radiation of the female blood.

12. The method according to claim 1,
wherein
the fluorescent intensity levels determined for a predefined spectral range from an established fluorescence intensity / wavenumber curves are defined in the evaluation unit as an integral intensity of the fluorescence radiation of the male blood and as an integral intensity of the fluorescence radiation of the female blood and Raman scattered radiation respectively overlapping the fluorescence radiation is defined for evaluation alone or in combination with other defined fluorescent intensity levels and assigned values, wherein if the fluorescent intensity levels and assigned values are combined, the Raman scatter radiation and the fluorescence radiation are evaluated together by a logical operation.

13. The method according to claim 1,
wherein,
if a pulsed laser beam from the laser beam source is used, the fluorescence intensity generated is measured in a time-resolved manner and, from a time constant T of a decay curve of the time-resolved fluorescence intensity, a sex determination is carried out, wherein a different time constant $T_{male}$, $T_{female}$, with $T_{male} \neq T_{female}$, is respectively determined for male blood and for female blood in order to determine the sex.

14. A device for optical in ovo sex determination of fertilized and incubated birds' eggs based on generated backscatter radiation using a method according to claim 1, wherein the device comprises
an egg-mounting unit, on which the egg is mounted;
a position-evaluation device which is connected to the egg-mounting unit;
a radiation device with light in a visible wavelength range for irradiating at least one blood vessel or a heart of an embryo;
a visible or green light detector detecting the at least one blood vessel or the heart of the embryo, wherein the visible or green light detector is connected to a positioning evaluation device;
a laser light device introducing laser light into the egg, which laser light device is at least connected to
at least one laser source emitting laser light;
at least one detector for recording fluorescence radiation;
a control unit for XYZ-positioning of the device onto a hole created in the egg;
a sex-determination evaluation unit that is connected to an amplification and detection unit and to the positioning evaluation unit, which is connected to a control unit;
wherein
a beam separating device (11) for separating the fluorescence radiation from backscatter radiation is arranged between a collimator collimating the laser beam and the laser light device introducing the laser light into the egg, wherein between the beam-separating device and at least one fluorescence detector, respectively, one beam path-specific detection filter for transmission of the fluorescence radiation is integrated,
wherein in the sex-determination evaluation unit an evaluation of the backscatter radiation, including the fluorescence radiation, from a recorded spectral intensity of the fluorescence radiation in a spectral range redshifted to an excitation wavelength, wherein sex-specific properties of the male blood and of the female blood are contained in the recorded spectral intensity and in a spectral profile of the recorded fluorescence radiation, and wherein at least one of intensity level determined from measured spectral intensities of the fluorescence radiation, or the values assigned thereto, for the male blood has an evaluable value distinct from at least one determined intensity level, or the values assigned thereto, for the female blood in the blood vessels or in the heart;

a determination of the sex of the bird egg from a difference of at least one of the values of the fluorescence intensity levels, or the values assigned thereto, and/or from a comparison with a predefined threshold value in the evaluation unit.

15. The device according to claim 14, wherein the laser beam that is produced in the laser source is transmitted by mirrors or fiber optics, wherein the laser beam is collimated with a collimator.

16. The device according to claim 14, wherein the light in the visible wavelength range, with which the radiation device of a vision system is provided in order to irradiate at least one blood vessel or the heart, is green light.

17. The device according to claim 14, wherein the visible or green light detector is configured to detect light in a visible wavelength range or in a green wavelength range is a camera.

18. The device according to claim 14, wherein the beam separation device for separating the fluorescence radiation from the backscatter radiation is a beam splitter.

19. The device according to claim 14, wherein, in the evaluation unit, the evaluation of the backscatter radiation, including the fluorescence radiation, occurs from the recorded spectral intensity of the fluorescence radiation in the spectral range redshifted to the excitation wavelength, wherein the sex-specific properties of the male blood and the female blood are contained in the recorded spectral intensity and in the spectral profile of the recorded fluorescence radiation, and wherein at least one of the intensity level determined from the measured spectral intensities of the fluorescence radiation, or the values assigned thereto, for the male blood has the evaluable value distinct from the at least one of the determined intensity levels, or the values assigned thereto, for the female blood in the blood vessels or for the heart;

a determination of the sex of the bird egg occurs from the difference of at least one of the values of the fluorescence intensity levels, or the values assigned thereto, and/or from the comparison with the predefined threshold value with programming and/or optional logical operations present in the evaluation unit.

20. The device according to claim 14, wherein the evaluation unit comprises, for a logical linking of intensity levels and assigned values or values derived from the intensity levels, at least one of an executable program configured to perform at least one logical operation or logical elements embodied as hardware for performing at least one logical operation.

21. A device for optical in ovo sex determination of fertilized and incubated birds' eggs based on generated backscatter radiation using a method according to claim 1, wherein the device comprises an egg-mounting unit, on which an egg is mounted;

a position-evaluation device which is connected to the egg-mounting unit;

a radiation device with light in a visible wavelength range for irradiating at least one blood-carrying blood vessel or a heart of an embryo;

a visible or green light detector detecting the at least one blood vessel or the heart of the embryo, wherein the visible or green light detector is connected to the positioning evaluation device;

a laser light device introducing laser light into the egg, which laser light device is at least connected to at least one laser beam source emitting laser light;

two or more detectors for recording the fluorescence radiation in two or more spectral ranges that are selected by predefined, beam path-specific bandpass filters;

a control unit for XYZ-positioning of the laser light device onto a hole created in the egg;

a sex-determination evaluation unit that is connected to an amplification and detection unit and to the positioning evaluation unit, which is connected to a control unit.

22. A device for optical in ovo sex determination of fertilized and incubated birds' eggs based on generated backscatter radiation using a method according to claim 1, wherein the device comprises:

an egg-mounting unit, on which an egg is mounted;

a position-evaluation device which is connected to the egg-mounting unit;

a radiation device with light in a visible wavelength range for irradiating at least one blood vessel or a heart of an embryo;

a visible or green light detector detecting the at least one blood vessel or the heart of the embryo, wherein the visible or green light detector is connected to the positioning evaluation device;

a laser light device for introducing laser light into the egg, which laser light device is at least connected to two or more laser beam sources emitting laser light;

two or more collimators, one for each laser beam source;

at least one beam coupler, with one each for each laser beam source;

two or more detectors for recording fluorescence radiation in two or more spectral ranges that are selected by adapted, beam path-specific bandpass filters;

a control unit for XYZ-positioning of the laser light device onto a hole created in the egg;

a sex-determination evaluation unit that is connected to a amplification and detection unit and to the positioning evaluation unit, which is connected to a control unit.

23. A device for optical in ovo sex determination of fertilized and incubated birds' eggs based on backscatter radiation, including fluorescence radiation, using a method according to claim 1, wherein the device comprises:

an egg-mounting unit, on which a egg is mounted;

a position-evaluation device which is connected to the egg-mounting unit;

a radiation device with light in a visible wavelength range for irradiating at least one blood vessel or a heart of an embryo;

a visible or green light detector detecting the at least one blood vessel or the heart of the embryo, wherein the visible or green light detector is connected to the positioning evaluation device;

a laser light device for introducing laser light into the egg, which laser light device is at least connected to a laser source emitting laser light;

a control unit for XYZ-positioning of the device onto a hole created in the egg;

a spectrometer for recording fluorescence radiation and overlapping Raman scattered radiation, wherein a notch filter is arranged in front of the spectrometer; and a sex-determination evaluation unit that is connected to a detection unit and to the positioning evaluation unit, which is connected to a control unit.

* * * * *